(12) United States Patent
Jackson

(10) Patent No.: US 9,414,863 B2
(45) Date of Patent: Aug. 16, 2016

(54) POLYAXIAL BONE SCREW WITH SPHERICAL CAPTURE, COMPRESSION INSERT AND ALIGNMENT AND RETENTION STRUCTURES

(76) Inventor: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 13/507,822

(22) Filed: Jul. 31, 2012

(65) Prior Publication Data
US 2012/0310290 A1   Dec. 6, 2012
US 2013/0274815 A9   Oct. 17, 2013

Related U.S. Application Data

(63) Continuation of application No. 12/072,354, filed on Feb. 26, 2008, now abandoned, which is a continuation-in-part of application No. 11/126,965, filed on May 10, 2005, now Pat. No. 7,476,239, and a
(Continued)

(51) Int. Cl.
*A61B 17/70* (2006.01)

(52) U.S. Cl.
CPC ......... *A61B 17/7037* (2013.01); *A61B 17/7032* (2013.01)

(58) Field of Classification Search
CPC ........... A61B 17/7037; A61B 17/7038; A61B 17/7032
USPC ......... 606/246, 250–253, 264–272, 300–309, 606/319
See application file for complete search history.

(56) References Cited

U.S. PATENT DOCUMENTS

| 791,548 A | 6/1905 | Fischer |
|---|---|---|
| 1,300,275 A | 4/1919 | Johnson |
| 1,330,673 A | 2/1920 | Anderson |
| 2,083,092 A | 1/1936 | Richer |
| 2,201,087 A | 5/1940 | Hallowell |
| 2,239,352 A | 4/1941 | Cherry |
| 2,243,717 A | 5/1941 | Moreira |
| 2,295,314 A | 9/1942 | Whitney |
| 2,346,346 A | 4/1944 | Anderson |

(Continued)

FOREIGN PATENT DOCUMENTS

| DE | 3630863 | 3/1988 |
|---|---|---|
| DE | 373809 | 5/1989 |

(Continued)

OTHER PUBLICATIONS

Brochure of Tyco/Healthcare/Surgical Dynamics on Spiral Radius 90D, Publication Date: Sep. 2001, pp. 1-8.
(Continued)

*Primary Examiner* — David Isabella
*Assistant Examiner* — Suba Ganesan
(74) *Attorney, Agent, or Firm* — Polsinelli PC

(57) ABSTRACT

A polyaxial bone screw assembly includes a receiver, a shank, an articulation structure for retaining the shank in the receiver and a compression insert for engagement with a longitudinal connecting member such as a rod. The articulation structure includes substantially spherical convex and concave surfaces that slidably engage both shank and receiver surfaces to provide compound articulation between the receiver and the shank. The receiver includes inwardly directed spring tabs engaging the insert and prohibiting rotation of the insert within the receiver.

44 Claims, 9 Drawing Sheets

Related U.S. Application Data continuation-in-part of application No. 12/008,067, filed on Jan. 8, 2008, now Pat. No. 7,901,437, said application No. 13/507,822 is a continuation-in-part of application No. 12/924,260, filed on Sep. 23, 2010, now Pat. No. 8,403,962, which is a continuation-in-part of application No. 11/385,957, filed on Mar. 21, 2006, now abandoned, which is a continuation-in-part of application No. 11/178,854, filed on Jul. 11, 2005, now Pat. No. 7,789,896.

(60) Provisional application No. 60/905,472, filed on Mar. 7, 2007, provisional application No. 60/897,723, filed on Jan. 26, 2007, provisional application No. 60/655,239, filed on Feb. 22, 2005.

(56) References Cited

U.S. PATENT DOCUMENTS

| | | |
|---|---|---|
| 2,362,999 A | 11/1944 | Elmer |
| 2,537,029 A | 8/1946 | Cambern |
| 2,445,978 A | 7/1948 | Stellin |
| 2,531,892 A | 11/1950 | Reese |
| 2,531,896 A | 11/1950 | Reese |
| 2,532,815 A | 12/1950 | Kindsvatter |
| 2,553,337 A | 5/1951 | Shafer |
| 2,778,265 A | 1/1957 | Brown |
| 2,813,450 A | 11/1957 | Dzus |
| 2,969,250 A | 1/1959 | Kull |
| 2,877,681 A | 3/1959 | Brown |
| 2,927,332 A | 3/1960 | Moore |
| 3,013,244 A | 12/1961 | Rudy |
| 3,143,029 A | 8/1964 | Brown |
| D200,217 S | 2/1965 | Curtiss |
| 3,236,275 A | 2/1966 | Smith |
| 3,370,341 A | 2/1968 | Allsop |
| 3,498,174 A | 3/1970 | Schuster et al. |
| 3,584,667 A | 6/1971 | Reiland |
| 3,604,487 A | 9/1971 | Gilbert |
| 3,640,416 A | 2/1972 | Temple |
| 3,812,757 A | 5/1974 | Reiland |
| 3,963,322 A | 6/1976 | Cryctko |
| 4,033,139 A | 7/1977 | Frederick |
| 4,041,939 A | 8/1977 | Hall |
| 4,103,422 A | 8/1978 | Weiss |
| 4,269,246 A | 5/1981 | Larson et al. |
| 4,369,769 A | 1/1983 | Edwards |
| 4,373,754 A | 2/1983 | Bollfrass et al. |
| 4,448,191 A | 5/1984 | Rodnyansky et al. |
| 4,484,570 A | 11/1984 | Sutter et al. |
| 4,492,500 A | 1/1985 | Ewing |
| 4,506,917 A | 3/1985 | Hansen Arne |
| 4,577,448 A | 3/1986 | Howorth |
| 4,600,224 A | 7/1986 | Blose |
| 4,641,636 A | 2/1987 | Cotrel |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,763,644 A | 8/1988 | Webb |
| 4,764,068 A | 8/1988 | Crispell |
| 4,790,297 A | 12/1988 | Luque |
| 4,805,602 A | 2/1989 | Puno et al. |
| 4,815,453 A | 3/1989 | Cotrel |
| 4,836,196 A | 6/1989 | Park et al. |
| 4,838,264 A | 6/1989 | Bremer et al. |
| 4,850,775 A | 7/1989 | Lee |
| 4,887,596 A | 12/1989 | Sherman |
| 4,946,458 A | 8/1990 | Harms et al. |
| 4,950,269 A | 8/1990 | Gaines, Jr. |
| 5,005,562 A | 4/1991 | Cotrel |
| 5,019,080 A | 5/1991 | Hemer |
| 5,022,791 A | 6/1991 | Isler |
| 5,026,373 A | 6/1991 | Ray et al. |
| 5,034,011 A | 7/1991 | Howland |
| 5,056,492 A | 10/1991 | Banse |
| 5,067,955 A | 11/1991 | Cotrel |
| 5,073,074 A | 12/1991 | Corrigan et al. |
| 5,092,635 A | 3/1992 | DeLange et al. |
| 5,102,412 A | 4/1992 | Rogozinski |
| 5,129,388 A | 7/1992 | Vignaud et al. |
| 5,129,899 A | 7/1992 | Small et al. |
| 5,147,360 A | 9/1992 | Dubousset |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,707 A | 2/1994 | Palm |
| 5,282,863 A | 2/1994 | Burton |
| 5,306,275 A | 4/1994 | Bryan |
| 5,312,404 A | 5/1994 | Asher et al. |
| 5,321,901 A | 6/1994 | Kelly |
| 5,334,203 A | 8/1994 | Wagner |
| 5,346,493 A | 9/1994 | Stahurski et al. |
| 5,354,299 A | 10/1994 | Coleman |
| 5,358,289 A | 10/1994 | Banker et al. |
| 5,360,431 A | 11/1994 | Puno et al. |
| 5,364,400 A | 11/1994 | Rego, Jr. et al. |
| 5,375,823 A | 12/1994 | Navas |
| 5,382,248 A | 1/1995 | Jacobson et al. |
| 5,385,583 A | 1/1995 | Cotrel |
| 5,387,212 A | 2/1995 | Yuan et al. |
| 5,395,371 A | 3/1995 | Miller et al. |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,551 A | 12/1995 | Finn et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,487,742 A | 1/1996 | Cotrel |
| 5,489,307 A | 2/1996 | Kuslich et al. |
| 5,490,750 A | 2/1996 | Gundy |
| 5,496,321 A | 3/1996 | Puno et al. |
| 5,499,892 A | 3/1996 | Reed |
| 5,507,745 A | 4/1996 | Logroscino et al. |
| 5,507,747 A | 4/1996 | Yuan et al. |
| 5,540,688 A | 7/1996 | Navas |
| 5,545,165 A | 8/1996 | Biedermann et al. |
| 5,554,157 A | 9/1996 | Errico et al. |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,591,235 A | 1/1997 | Kuslich |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,624,442 A | 4/1997 | Mellinger et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |

(56) References Cited

U.S. PATENT DOCUMENTS

| | | |
|---|---|---|
| 5,647,873 A | 7/1997 | Errico et al. |
| 5,653,710 A | 8/1997 | Harle |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,711,709 A | 1/1998 | McCoy |
| 5,713,705 A | 2/1998 | Grunbichler |
| 5,713,898 A | 2/1998 | Stucker et al. |
| 5,716,356 A | 2/1998 | Biedermann et al. |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,797,911 A | 8/1998 | Sherman et al. |
| 5,800,435 A | 9/1998 | Errico et al. |
| 5,800,547 A | 9/1998 | Schafer et al. |
| 5,817,094 A | 10/1998 | Errico et al. |
| 5,863,293 A | 1/1999 | Richelsoph |
| 5,873,878 A | 2/1999 | Harms et al. |
| D407,302 S | 3/1999 | Lawson |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,303 A | 5/1999 | Eckhof et al. |
| RE36,221 E | 6/1999 | Breard et al. |
| 5,910,142 A | 6/1999 | Tatar |
| 5,938,663 A | 8/1999 | Petreto |
| 5,944,465 A | 8/1999 | Janitzki |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,078 A | 4/2000 | Parker |
| 6,053,917 A | 4/2000 | Sherman et al. |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,139,550 A | 10/2000 | Michelson |
| 6,143,032 A | 11/2000 | Schafer et al. |
| 6,146,383 A | 11/2000 | Studer et al. |
| 6,149,533 A | 11/2000 | Finn |
| 6,183,472 B1 | 2/2001 | Lutz |
| 6,186,718 B1 | 2/2001 | Fogard |
| 6,187,005 B1 | 2/2001 | Brace et al. |
| 6,193,719 B1 | 2/2001 | Gournay et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,235,034 B1 | 5/2001 | Bray |
| 6,241,730 B1 | 6/2001 | Alby |
| 6,248,105 B1 | 6/2001 | Schlapfer et al. |
| 6,254,146 B1 | 7/2001 | Church |
| 6,254,602 B1 | 7/2001 | Justis |
| 6,261,039 B1 | 7/2001 | Reed |
| 6,267,764 B1 | 7/2001 | Elberg |
| 6,267,765 B1 | 7/2001 | Taylor et al. |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,302,888 B1 | 10/2001 | Mellinger et al. |
| 6,309,391 B1 | 10/2001 | Crandall et al. |
| 6,315,564 B1 | 11/2001 | Levisman |
| 6,322,108 B1 | 11/2001 | Riesselmann et al. |
| 6,331,179 B1 | 12/2001 | Freid et al. |
| 6,349,794 B2 | 2/2002 | Spencer |
| 6,355,040 B1 | 3/2002 | Richelsoph et al. |
| 6,361,535 B2 | 3/2002 | Jackson |
| RE37,665 E | 4/2002 | Ralph et al. |
| 6,368,321 B1 | 4/2002 | Jackson |
| 6,371,957 B1 | 4/2002 | Amrein et al. |
| 6,375,657 B1 | 4/2002 | Doubler et al. |
| 6,402,752 B2 | 6/2002 | Schaffler-Wachter et al. |
| 6,402,757 B1 | 6/2002 | Moore et al. |
| 6,432,109 B1 | 8/2002 | Letendart et al. |
| 6,440,135 B2 | 8/2002 | Orgay et al. |
| 6,440,137 B1 | 8/2002 | Horvath et al. |
| 6,443,953 B1 | 9/2002 | Perra et al. |
| 6,451,021 B1 | 9/2002 | Ralph et al. |
| 6,454,772 B1 | 9/2002 | Jackson |
| 6,471,703 B1 | 10/2002 | Ashman |
| 6,471,705 B1 | 10/2002 | Biedermann et al. |
| 6,485,491 B1 | 11/2002 | Farris et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,520,963 B1 | 2/2003 | McKinley |
| 6,527,804 B1 | 3/2003 | Gauchet et al. |
| 6,530,929 B1 | 3/2003 | Jusis et al. |
| 6,533,786 B1 | 3/2003 | Needham et al. |
| 6,540,749 B2 | 4/2003 | Schafer et al. |
| 6,547,790 B2 | 4/2003 | Harkey, III et al. |
| 6,551,320 B2 | 4/2003 | Liebermann |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,602,255 B1 | 8/2003 | Campbell |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |

(56) References Cited

U.S. PATENT DOCUMENTS

| | | |
|---|---|---|
| 6,652,526 B1 | 11/2003 | Arafiles |
| 6,652,765 B1 | 11/2003 | Beaty |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,692,500 B2 | 2/2004 | Reed |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,726,689 B2 | 4/2004 | Jackson |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,783,527 B2 | 8/2004 | Drewry et al. |
| 6,790,209 B2 | 9/2004 | Beale et al. |
| 6,802,844 B2 | 10/2004 | Ferree |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 * | 3/2005 | Glascott ............... 606/308 |
| 6,872,208 B1 | 3/2005 | McBride et al. |
| 6,896,676 B2 | 5/2005 | Zubok et al. |
| 6,896,677 B1 | 5/2005 | Lin |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| RE39,035 E | 3/2006 | Finn et al. |
| 7,008,424 B2 | 3/2006 | Teitelbaum |
| 7,018,378 B2 | 3/2006 | Biedermann et al. |
| 7,018,379 B2 | 3/2006 | Drewry et al. |
| 7,022,122 B2 | 4/2006 | Amrein et al. |
| 7,029,475 B2 | 4/2006 | Panjabi |
| RE39,089 E | 5/2006 | Ralph et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,144,396 B2 | 12/2006 | Shluzas |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,186,255 B2 | 3/2007 | Baynham et al. |
| 7,207,992 B2 | 4/2007 | Ritland |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,229,441 B2 | 6/2007 | Trieu et al. |
| 7,264,621 B2 | 9/2007 | Coates et al. |
| 7,270,665 B2 | 9/2007 | Morrison et al. |
| 7,291,151 B2 | 11/2007 | Alvarez |
| 7,291,153 B2 | 11/2007 | Glascott |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,445,627 B2 * | 11/2008 | Hawkes et al. ............... 606/269 |
| 7,476,228 B2 | 1/2009 | Abdou |
| 7,479,156 B2 | 1/2009 | Lourdel et al. |
| 7,491,218 B2 | 2/2009 | Landry et al. |
| 7,491,221 B2 | 2/2009 | David |
| 7,503,918 B2 | 3/2009 | Baccelli et al. |
| 7,503,924 B2 | 3/2009 | Lee et al. |
| 7,524,323 B2 | 4/2009 | Malandain |
| 7,527,640 B2 | 5/2009 | Ziolo et al. |
| 7,530,992 B2 | 5/2009 | Biedermann et al. |
| 7,559,943 B2 | 7/2009 | Mjuwid |
| 7,563,264 B2 | 7/2009 | Landry et al. |
| 7,563,275 B2 | 7/2009 | Falahee et al. |
| 7,569,061 B2 | 8/2009 | Colleran |
| 7,569,068 B2 | 8/2009 | Ramare |
| 7,572,280 B2 | 8/2009 | Dickinson et al. |
| 7,575,587 B2 | 8/2009 | Rezach et al. |
| 7,588,575 B2 | 9/2009 | Colleran et al. |
| 7,588,588 B2 | 9/2009 | Spitler et al. |
| 7,588,593 B2 | 9/2009 | Aferzon |
| 7,591,839 B2 | 9/2009 | Biedermann et al. |
| 7,601,166 B2 | 10/2009 | Biedermann et al. |
| 7,604,656 B2 | 10/2009 | Shluzas |
| 7,611,518 B2 | 11/2009 | Walder et al. |
| 7,615,068 B2 | 11/2009 | Timm et al. |
| 7,621,941 B2 | 11/2009 | Schlapfer et al. |
| 7,625,394 B2 | 12/2009 | Molz, IV et al. |
| 7,641,674 B2 | 1/2010 | Young |
| 7,645,294 B2 | 1/2010 | Kalfas et al. |
| 7,648,522 B2 | 1/2010 | David |
| 2001/0001119 A1 | 5/2001 | Lombardo |
| 2001/0037111 A1 | 11/2001 | Dixon et al. |
| 2002/0007184 A1 | 1/2002 | Ogilvie et al. |
| 2002/0013586 A1 | 1/2002 | Justis et al. |
| 2002/0026193 A1 | 2/2002 | Barker et al. |
| 2002/0035366 A1 | 3/2002 | Walder et al. |
| 2002/0045898 A1 | 4/2002 | Freid et al. |
| 2002/0058942 A1 | 5/2002 | Biedermann et al. |

(56) References Cited

U.S. PATENT DOCUMENTS

| | | |
|---|---|---|
| 2002/0072751 A1 | 6/2002 | Jackson |
| 2002/0082602 A1 | 6/2002 | Biedermann et al. |
| 2002/0111626 A1 | 8/2002 | Ralph et al. |
| 2002/0133154 A1 | 9/2002 | Saint Martin |
| 2002/0133158 A1 | 9/2002 | Saint Martin |
| 2002/0133159 A1 | 9/2002 | Jackson |
| 2002/0143341 A1 | 10/2002 | Biedermann |
| 2002/0173789 A1 | 11/2002 | Howland |
| 2002/0193795 A1 | 12/2002 | Gertzbein et al. |
| 2003/0004512 A1 | 1/2003 | Farris et al. |
| 2003/0023240 A1 | 1/2003 | Amrein et al. |
| 2003/0023243 A1 | 1/2003 | Biedermann et al. |
| 2003/0028191 A1 | 2/2003 | Shluzas |
| 2003/0073996 A1 | 4/2003 | Doubler et al. |
| 2003/0083657 A1 | 5/2003 | Drewry et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann et al. |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0171749 A1 | 9/2003 | Le Couedic et al. |
| 2003/0176862 A1 | 9/2003 | Taylor et al. |
| 2003/0191470 A1 | 10/2003 | Ritland |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2003/0220642 A1 | 11/2003 | Freudiger |
| 2003/0220643 A1 | 11/2003 | Ferree |
| 2004/0002708 A1 | 1/2004 | Ritland |
| 2004/0006342 A1 | 1/2004 | Altarac et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0078082 A1 | 4/2004 | Lange |
| 2004/0087949 A1 | 5/2004 | Bono et al. |
| 2004/0087952 A1 | 5/2004 | Borgstrom et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0153068 A1 | 8/2004 | Janowski |
| 2004/0158247 A1 | 8/2004 | Sitiso et al. |
| 2004/0162560 A1 | 8/2004 | Raynor et al. |
| 2004/0172022 A1 | 9/2004 | Landry et al. |
| 2004/0172032 A1 | 9/2004 | Jackson |
| 2004/0176766 A1 | 9/2004 | Shluzas |
| 2004/0186473 A1 | 9/2004 | Coumoyer et al. |
| 2004/0193160 A1* | 9/2004 | Richelsoph ............... 606/61 |
| 2004/0210216 A1 | 10/2004 | Farris et al. |
| 2004/0225289 A1 | 11/2004 | Biedermann et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0033298 A1 | 2/2005 | Hawkes et al. |
| 2005/0038432 A1 | 2/2005 | Shaolian et al. |
| 2005/0049589 A1 | 3/2005 | Jackson |
| 2005/0049708 A1 | 3/2005 | Atkinson et al. |
| 2005/0055026 A1 | 3/2005 | Biedermann et al. |
| 2005/0065515 A1 | 3/2005 | Jahng |
| 2005/0065516 A1 | 3/2005 | Jahng |
| 2005/0070899 A1 | 3/2005 | Doubler et al. |
| 2005/0080415 A1 | 4/2005 | Keyer et al. |
| 2005/0085812 A1 | 4/2005 | Sherman et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0096653 A1 | 5/2005 | Doubler |
| 2005/0096654 A1 | 5/2005 | Lin |
| 2005/0107788 A1 | 5/2005 | Beaurain et al. |
| 2005/0113927 A1 | 5/2005 | Malek |
| 2005/0124991 A1 | 6/2005 | Jahng |
| 2005/0131404 A1 | 6/2005 | Mazda et al. |
| 2005/0131407 A1 | 6/2005 | Sicvol et al. |
| 2005/0131413 A1 | 6/2005 | O'Driscoll et al. |
| 2005/0137597 A1 | 6/2005 | Butler et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171542 A1 | 8/2005 | Biederman et al. |
| 2005/0171543 A1 | 8/2005 | Timm et al. |
| 2005/0177157 A1 | 8/2005 | Jahng |
| 2005/0182401 A1 | 8/2005 | Timm et al. |
| 2005/0182410 A1 | 8/2005 | Jackson |
| 2005/0187548 A1 | 8/2005 | Butler et al. |
| 2005/0187555 A1 | 8/2005 | Biedermann et al. |
| 2005/0192580 A1 | 9/2005 | Dalton |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0216001 A1 | 9/2005 | David |
| 2005/0216003 A1 | 9/2005 | Biedermann et al. |
| 2005/0228379 A1 | 10/2005 | Jackson |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251140 A1 | 11/2005 | Shaolian et al. |
| 2005/0251141 A1 | 11/2005 | Frigg et al. |
| 2005/0260058 A1 | 11/2005 | Casagne, III |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |

(56) References Cited

U.S. PATENT DOCUMENTS

| | | |
|---|---|---|
| 2006/0009767 A1 | 1/2006 | Kiester |
| 2006/0009768 A1 | 1/2006 | Ritland |
| 2006/0009769 A1 | 1/2006 | Liebermann |
| 2006/0009770 A1 | 1/2006 | Speirs et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0025771 A1 | 2/2006 | Jackson |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak |
| 2006/0079898 A1 | 4/2006 | Ainsworth |
| 2006/0079899 A1 | 4/2006 | Ritland |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0089643 A1 | 4/2006 | Mujwid |
| 2006/0089644 A1 | 4/2006 | Felix |
| 2006/0095037 A1 | 5/2006 | Jones et al. |
| 2006/0100621 A1 | 5/2006 | Jackson |
| 2006/0106380 A1 | 5/2006 | Colleran et al. |
| 2006/0106381 A1 | 5/2006 | Ferree |
| 2006/0106383 A1 | 5/2006 | Biedermann et al. |
| 2006/0116677 A1 | 6/2006 | Burd et al. |
| 2006/0122599 A1 | 6/2006 | Drewry |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0142761 A1 | 6/2006 | Landry et al. |
| 2006/0149228 A1 | 7/2006 | Schlapfer |
| 2006/0149229 A1 | 7/2006 | Kwak |
| 2006/0149232 A1 | 7/2006 | Sasing |
| 2006/0149238 A1 | 7/2006 | Sherman et al. |
| 2006/0149241 A1 | 7/2006 | Richelsoph et al. |
| 2006/0149244 A1 | 7/2006 | Amrein et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189984 A1 | 8/2006 | Fallin |
| 2006/0189985 A1 | 8/2006 | Lewis |
| 2006/0195090 A1 | 8/2006 | Suddaby |
| 2006/0195093 A1 | 8/2006 | Jahng |
| 2006/0195098 A1 | 8/2006 | Schumacher |
| 2006/0200128 A1 | 9/2006 | Mueller |
| 2006/0200130 A1 | 9/2006 | Hawkins |
| 2006/0200131 A1 | 9/2006 | Chao et al. |
| 2006/0200149 A1 | 9/2006 | Hoy et al. |
| 2006/0212033 A1 | 9/2006 | Rothman |
| 2006/0212034 A1 | 9/2006 | Triplett et al. |
| 2006/0217716 A1 | 9/2006 | Baker et al. |
| 2006/0229608 A1 | 10/2006 | Foster |
| 2006/0229609 A1 | 10/2006 | Wang |
| 2006/0229612 A1 | 10/2006 | Rothman |
| 2006/0229613 A1 | 10/2006 | Timm |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241769 A1 | 10/2006 | Gordon |
| 2006/0241771 A1 | 10/2006 | Gordon |
| 2006/0247624 A1 | 11/2006 | Banouskou et al. |
| 2006/0247631 A1 | 11/2006 | Ahn et al. |
| 2006/0247632 A1 | 11/2006 | Winslow |
| 2006/0247633 A1 | 11/2006 | Winslow |
| 2006/0247635 A1 | 11/2006 | Gordon |
| 2006/0247636 A1 | 11/2006 | Yuan et al. |
| 2006/0247637 A1 | 11/2006 | Colleran |
| 2006/0247779 A1 | 11/2006 | Gordon et al. |
| 2006/0264933 A1 | 11/2006 | Baker et al. |
| 2006/0264936 A1 | 11/2006 | Partin et al. |
| 2006/0264937 A1 | 11/2006 | White |
| 2006/0264940 A1 | 11/2006 | Hartmannt |
| 2006/0271051 A1 | 11/2006 | Berrevoets et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0282075 A1 | 12/2006 | Labrom |
| 2006/0282076 A1 | 12/2006 | Labrom |
| 2006/0282077 A1 | 12/2006 | Labrom |
| 2006/0282078 A1 | 12/2006 | Labrom |
| 2006/0282079 A1 | 12/2006 | Labrom |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293665 A1 | 12/2006 | Shluzas |
| 2006/0293666 A1 | 12/2006 | Matthis et al. |
| 2007/0005062 A1 | 1/2007 | Lange |
| 2007/0005063 A1 | 1/2007 | Bruneau |
| 2007/0005137 A1 | 1/2007 | Kwak |
| 2007/0016188 A1 | 1/2007 | Boehm, Jr. et al. |
| 2007/0016190 A1 | 1/2007 | Martinez |
| 2007/0016193 A1 | 1/2007 | Ritland |
| 2007/0016198 A1 | 1/2007 | Boehm, Jr. et al. |
| 2007/0016200 A1 | 1/2007 | Jackson |
| 2007/0021750 A1 | 1/2007 | Shluzas et al. |
| 2007/0043355 A1 | 2/2007 | Bette et al. |
| 2007/0043356 A1 | 2/2007 | Timm |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049933 A1 | 3/2007 | Ahn et al. |
| 2007/0049936 A1 | 3/2007 | Colleran |
| 2007/0055235 A1 | 3/2007 | Janowski et al. |
| 2007/0055238 A1 | 3/2007 | Biedermann et al. |
| 2007/0055239 A1 | 3/2007 | Sweeney et al. |

(56) References Cited

U.S. PATENT DOCUMENTS

| | | |
|---|---|---|
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0055247 A1 | 3/2007 | Jahng |
| 2007/0073289 A1 | 3/2007 | Kwak |
| 2007/0073291 A1 | 3/2007 | Cordaro et al. |
| 2007/0073293 A1 | 3/2007 | Martz |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0093813 A1 | 4/2007 | Callahan et al. |
| 2007/0093814 A1 | 4/2007 | Callahan, II et al. |
| 2007/0093815 A1 | 4/2007 | Callahan, II et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093826 A1 | 4/2007 | Hawkes et al. |
| 2007/0093827 A1 | 4/2007 | Warnick |
| 2007/0093831 A1 | 4/2007 | Abdelgany et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123864 A1 | 5/2007 | Walder et al. |
| 2007/0123865 A1 | 5/2007 | Schlapfer et al. |
| 2007/0123866 A1 | 5/2007 | Gerbec et al. |
| 2007/0123867 A1 | 5/2007 | Kirschman |
| 2007/0123870 A1 | 5/2007 | Jeon et al. |
| 2007/0123871 A1 | 5/2007 | Jahng |
| 2007/0129729 A1 | 6/2007 | Petit et al. |
| 2007/0135815 A1 | 6/2007 | Gerbec et al. |
| 2007/0161986 A1 | 7/2007 | Levy |
| 2007/0161991 A1 | 7/2007 | Altarac et al. |
| 2007/0161994 A1 | 7/2007 | Lowrey et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0225707 A1 | 9/2007 | Wisnewski et al. |
| 2007/0225708 A1 | 9/2007 | Biedermann et al. |
| 2007/0225710 A1 | 9/2007 | Jahng et al. |
| 2007/0225711 A1 | 9/2007 | Ensign |
| 2007/0233073 A1 | 10/2007 | Wisnewski et al. |
| 2007/0233075 A1 | 10/2007 | Dawson |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233087 A1 | 10/2007 | Schlapfer |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0250061 A1 | 10/2007 | Chin et al. |
| 2007/0260246 A1 | 11/2007 | Biedermann |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270815 A1 | 11/2007 | Johnson et al. |
| 2007/0270830 A1 | 11/2007 | Morrison |
| 2007/0270831 A1 | 11/2007 | Dewey et al. |
| 2007/0270832 A1 | 11/2007 | Moore |
| 2007/0270835 A1 | 11/2007 | Wisnewski |
| 2007/0270839 A1* | 11/2007 | Jeon et al. ............... 606/61 |
| 2007/0288004 A1 | 12/2007 | Alvarez |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021462 A1 | 1/2008 | Trieu |
| 2008/0021464 A1 | 1/2008 | Morin et al. |
| 2008/0021473 A1 | 1/2008 | Butler et al. |
| 2008/0027432 A1 | 1/2008 | Strauss et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0058811 A1 | 3/2008 | Alleyne et al. |
| 2008/0058812 A1 | 3/2008 | Zehnder |
| 2008/0065073 A1 | 3/2008 | Perriello et al. |
| 2008/0065075 A1 | 3/2008 | Dant |
| 2008/0065077 A1 | 3/2008 | Ferree |
| 2008/0071273 A1 | 3/2008 | Hawkes et al. |
| 2008/0071274 A1 | 3/2008 | Enisgn |
| 2008/0071277 A1 | 3/2008 | Warnick |
| 2008/0077139 A1 | 3/2008 | Landry et al. |
| 2008/0086131 A1 | 4/2008 | Daly et al. |
| 2008/0086132 A1 | 4/2008 | Biedermann et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0119858 A1 | 5/2008 | Potash |
| 2008/0140075 A1 | 6/2008 | Ensign et al. |
| 2008/0161859 A1 | 7/2008 | Nilsson |
| 2008/0161863 A1 | 7/2008 | Arnold et al. |
| 2008/0177321 A1 | 7/2008 | Drewry et al. |
| 2008/0177322 A1 | 7/2008 | Davis et al. |
| 2008/0177332 A1 | 7/2008 | Reiley et al. |
| 2008/0183215 A1 | 7/2008 | Altarac et al. |
| 2008/0183223 A1 | 7/2008 | Jeon et al. |
| 2008/0195159 A1 | 8/2008 | Kloss et al. |
| 2008/0200956 A1 | 8/2008 | Beckwith et al. |
| 2008/0215095 A1 | 9/2008 | Biedermann et al. |
| 2008/0228229 A1 | 9/2008 | Walder et al. |
| 2008/0234734 A1 | 9/2008 | Walder et al. |
| 2008/0234756 A1 | 9/2008 | Sutcliffe et al. |
| 2008/0234759 A1 | 9/2008 | Marino |
| 2008/0249570 A1 | 10/2008 | Carson et al. |
| 2008/0262548 A1 | 10/2008 | Lange et al. |
| 2008/0262556 A1 | 10/2008 | Jacofsky et al. |
| 2008/0269742 A1 | 10/2008 | Levy et al. |
| 2008/0269809 A1 | 10/2008 | Garamszegi |
| 2008/0287994 A1 | 11/2008 | Perez-Cruet et al. |
| 2008/0288002 A1 | 11/2008 | Crall et al. |
| 2008/0306528 A1 | 12/2008 | Winslow et al. |
| 2008/0306533 A1 | 12/2008 | Winslow et al. |
| 2008/0306539 A1 | 12/2008 | Cain et al. |
| 2008/0312655 A1 | 12/2008 | Kirschman et al. |
| 2008/0312692 A1 | 12/2008 | Brennan et al. |
| 2008/0312696 A1 | 12/2008 | Battlers et al. |
| 2008/0312701 A1 | 12/2008 | Batters et al. |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0012567 A1 | 1/2009 | Biedermann et al. |
| 2009/0018591 A1 | 1/2009 | Hawkes et al. |

(56) References Cited

U.S. PATENT DOCUMENTS

| | | | |
|---|---|---|---|
| 2009/0024169 A1 | 1/2009 | Triplett et al. |
| 2009/0030457 A1 | 1/2009 | Janowski et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0062860 A1 | 3/2009 | Fraiser et al. |
| 2009/0062865 A1 | 3/2009 | Schumacher |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082809 A1 | 3/2009 | Nguyen et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088799 A1 | 4/2009 | Yeh |
| 2009/0088807 A1 | 4/2009 | Castaneda et al. |
| 2009/0093843 A1 | 4/2009 | Lemoine et al. |
| 2009/0105769 A1 | 4/2009 | Rock et al. |
| 2009/0105770 A1 | 4/2009 | Berrevoets et al. |
| 2009/0105771 A1 | 4/2009 | Lei et al. |
| 2009/0118772 A1 | 5/2009 | Diederich et al. |
| 2009/0131983 A1 | 5/2009 | Biedermann |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143829 A1 | 6/2009 | Shluzas |
| 2009/0149887 A1 | 6/2009 | Schlaepfer et al. |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0182380 A1 | 7/2009 | Abdelgany |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198289 A1 | 8/2009 | Manderson |
| 2009/0198291 A1 | 8/2009 | Kevin et al. |
| 2009/0204155 A1 | 8/2009 | Aschmann |
| 2009/0216280 A1 | 8/2009 | Hutchinson |
| 2009/0248030 A1 | 10/2009 | Butler et al. |
| 2009/0248075 A1 | 10/2009 | Ogilvie et al. |
| 2009/0248088 A1 | 10/2009 | Biedermann |
| 2009/0254125 A1 | 10/2009 | Predick |
| 2009/0259254 A1 | 10/2009 | Pisharodi |
| 2009/0264896 A1 | 10/2009 | Biedermann et al. |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0287253 A1 | 11/2009 | Felix et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0326582 A1 | 12/2009 | Songer et al. |
| 2009/0326587 A1 | 12/2009 | Matthis et al. |
| 2010/0004692 A1 | 1/2010 | Biedermann et al. |
| 2010/0010540 A1 | 1/2010 | Park |
| 2010/0016898 A1 | 1/2010 | Shluzas |
| 2010/0256684 A1 | 10/2010 | Seme et al. |

FOREIGN PATENT DOCUMENTS

| | | |
|---|---|---|
| DE | 9202745 | 4/1992 |
| DE | 4425392 | 11/1995 |
| DE | 19507141 | 9/1996 |
| DE | 19509331 | 9/1996 |
| DE | 29806563 | 7/1998 |
| DE | 28910798 | 12/1999 |
| DE | 29810798 | 12/1999 |
| DE | 19951145 | 5/2001 |
| DE | 10157969 | 2/2003 |
| EP | 0195455 | 9/1986 |
| EP | 0172130 | 2/1987 |
| EP | 0276153 | 7/1988 |
| EP | 0465158 | 1/1992 |
| EP | 0667127 | 8/1995 |
| EP | 0677277 | 10/1995 |
| EP | 0885598 | 12/1998 |
| EP | 1090595 | 4/2001 |
| EP | 1121902 | 8/2001 |
| EP | 1190678 | 3/2002 |
| EP | 1210914 | 6/2002 |
| EP | 1277444 | 1/2003 |
| EP | 1449486 | 8/2004 |
| EP | 1570795 | 9/2005 |
| EP | 1579816 | 9/2005 |
| EP | 1634537 | 3/2006 |
| EP | 1925263 | 5/2008 |
| FR | 2467312 | 4/1981 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| FR | 2925288 | 6/2009 |
| GB | 203508 | 9/1923 |
| GB | 2082709 | 3/1982 |
| GB | 2140523 | 11/1984 |
| GB | 9202745.8 | 4/1992 |
| GB | 2365345 | 2/2002 |
| GB | 2382304 | 5/2003 |
| JP | 9-504727 | 5/1997 |
| JP | 2000325358 | 3/2000 |
| SU | 371359 | 8/1973 |
| WO | WO92/03100 | 3/1992 |
| WO | WO94/10927 | 5/1994 |
| WO | WO94/10944 | 5/1994 |
| WO | WO94/26191 | 11/1994 |
| WO | WO95/01132 | 1/1995 |
| WO | WO95/35067 | 12/1995 |
| WO | WO96/06576 | 3/1996 |
| WO | WO96/28118 | 9/1996 |
| WO | WO97/14366 | 4/1997 |
| WO | WO98/32386 | 7/1998 |
| WO | WO01/45576 | 6/2001 |
| WO | WO01/49191 | 7/2001 |
| WO | WO02/054966 | 7/2002 |
| WO | WO02/102259 | 12/2002 |
| WO | WO03/026523 | 4/2003 |
| WO | WO03/068088 | 8/2003 |
| WO | WO2004/021900 | 3/2004 |
| WO | WO2004/041100 | 5/2004 |
| WO | WO2004/075778 | 9/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/065374 | 7/2005 |
| WO | WO2005/065375 | 7/2005 |
| WO | WO2005/072632 | 8/2005 |
| WO | WO2005/082262 | 9/2005 |
| WO | WO2005/099400 | 10/2005 |
| WO | WO2005/104969 | 11/2005 |
| WO | WO2006/005198 | 1/2006 |
| WO | WO2006/012088 | 2/2006 |
| WO | WO2006/017616 | 2/2006 |
| WO | WO2006/028537 | 3/2006 |
| WO | WO2006/119241 | 11/2006 |
| WO | WO2007/118045 | 10/2007 |

(56) References Cited

FOREIGN PATENT DOCUMENTS

| WO | WO2007/124222 | 11/2007 |
|---|---|---|
| WO | WO2007/0124249 | 11/2007 |
| WO | WO2007/124249 | 11/2007 |
| WO | WO2007/0130835 | 11/2007 |
| WO | WO2007/130840 | 11/2007 |
| WO | WO2007/130941 | 11/2007 |
| WO | WO2008/088731 | 7/2008 |
| WO | WO2009/015100 | 1/2009 |

OTHER PUBLICATIONS

Spine, Lipcott, Williams & Wilkins, Inc. vol. 24, No. 15, p. 1495.
*EBI Omega 21* Brochure, EBI Spine Systems, pub. 1999.
*Claris Instrumentation* Brochure, G Med, pub. 1997.
*VLS System Variable Locking Screw* Brochure, Interpore Cross International, 1999.
*CD Horizon M8 Multi Axial Screw Spinal System* Brochure, Medtronic Sofamor Danek, no publish date.
*Contour Spinal System* Brochure, Ortho Development, no publish date.
*Xia Spinal System* Brochure, Stryker Howmedica Osteonics, no publish date.
*The Rod Plate System* Brochure, Stryker Howmedica Osteonics, pub. Oct. 1999.
*Silhouette Spinal Fixation* System Brochure, Sulzer Medica Spine—Tech, no publish date.
*SDRS Surgical Dynamics Rod System* Brochure, Surgical Dynamics, pub. 1998-99.
*Versalok Low Back Fixation System* Brochure, Wright Medical Technology, Inc., pub. 1997.
*The Strength of Innovation* Advertisement, Blackstone Medical Inc., no publish date.
*The Moss Miami 6.0mm System* Advertisement, author unknown, no publish date.

* cited by examiner

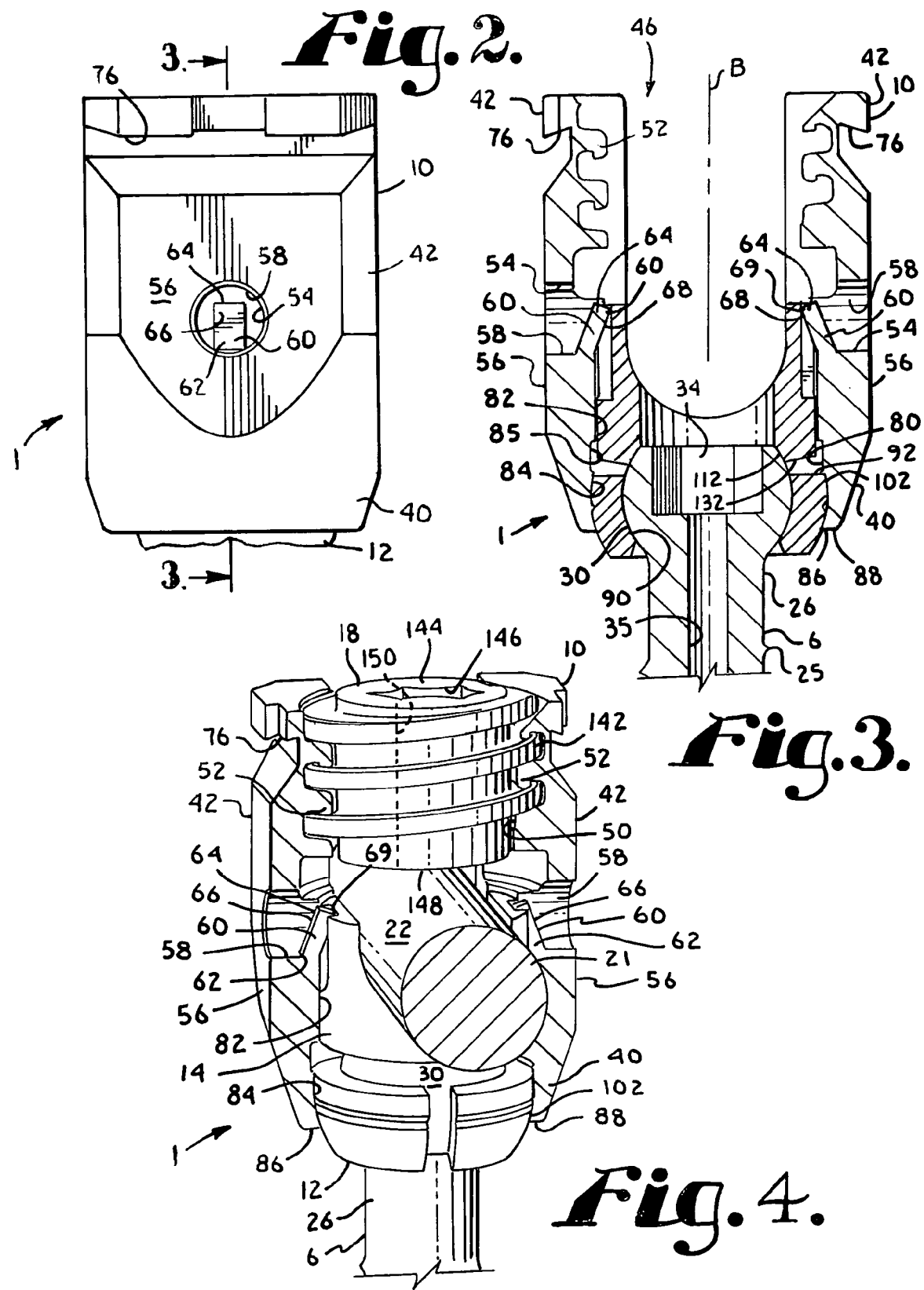

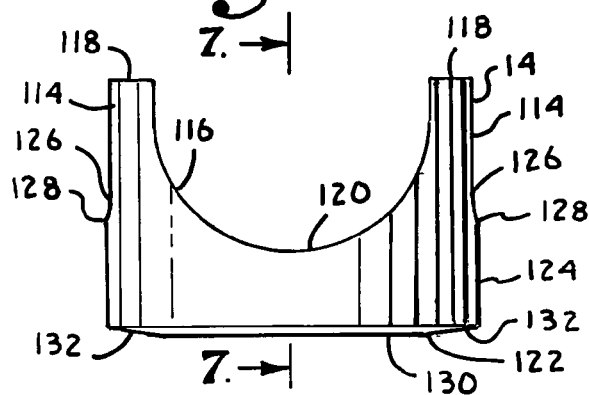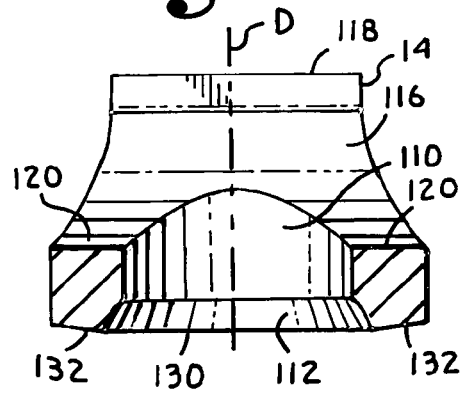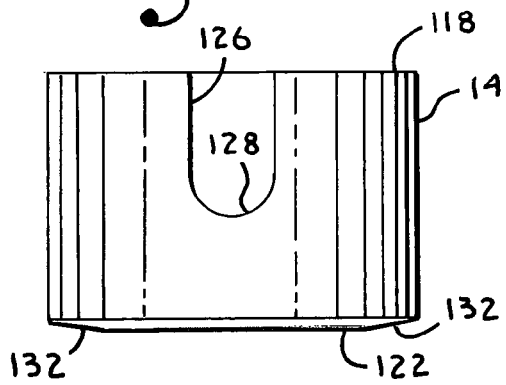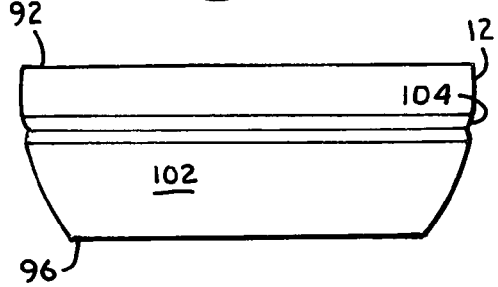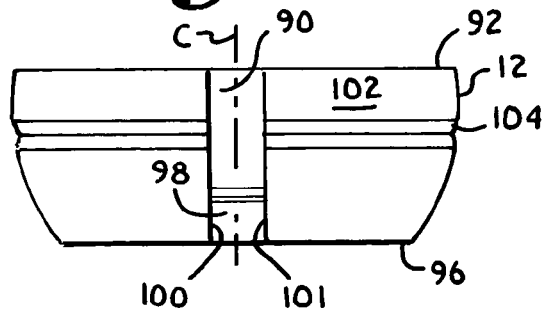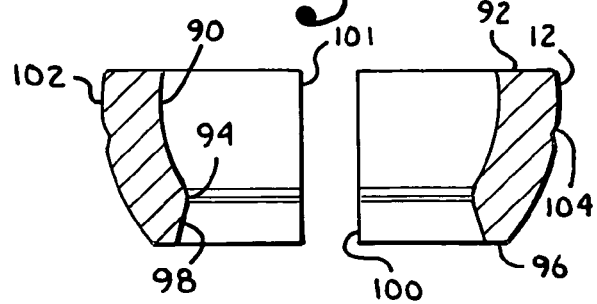

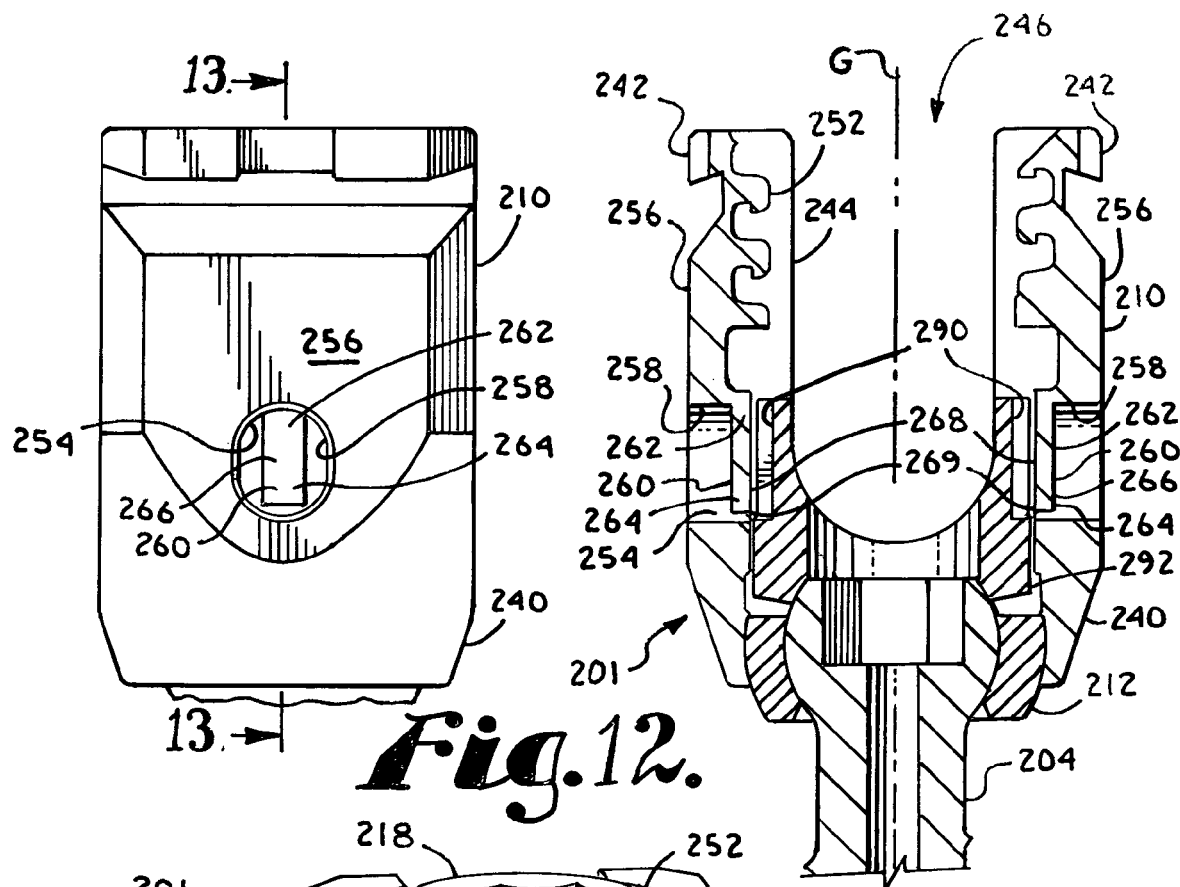
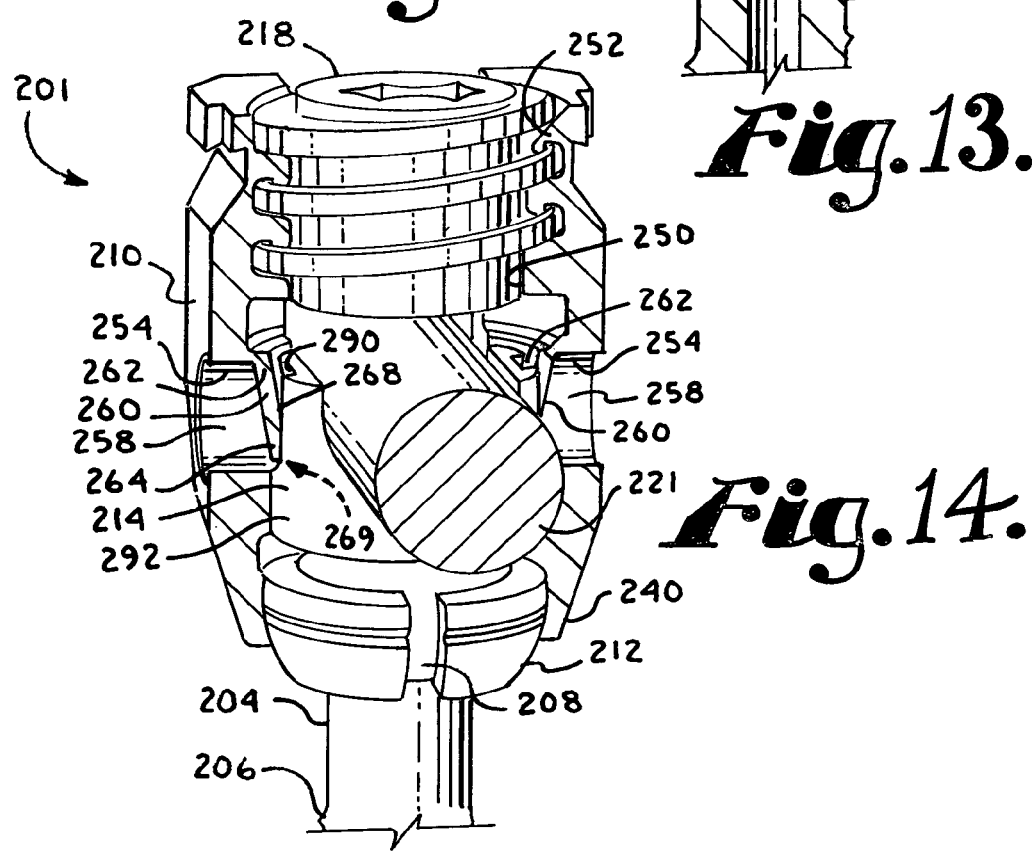

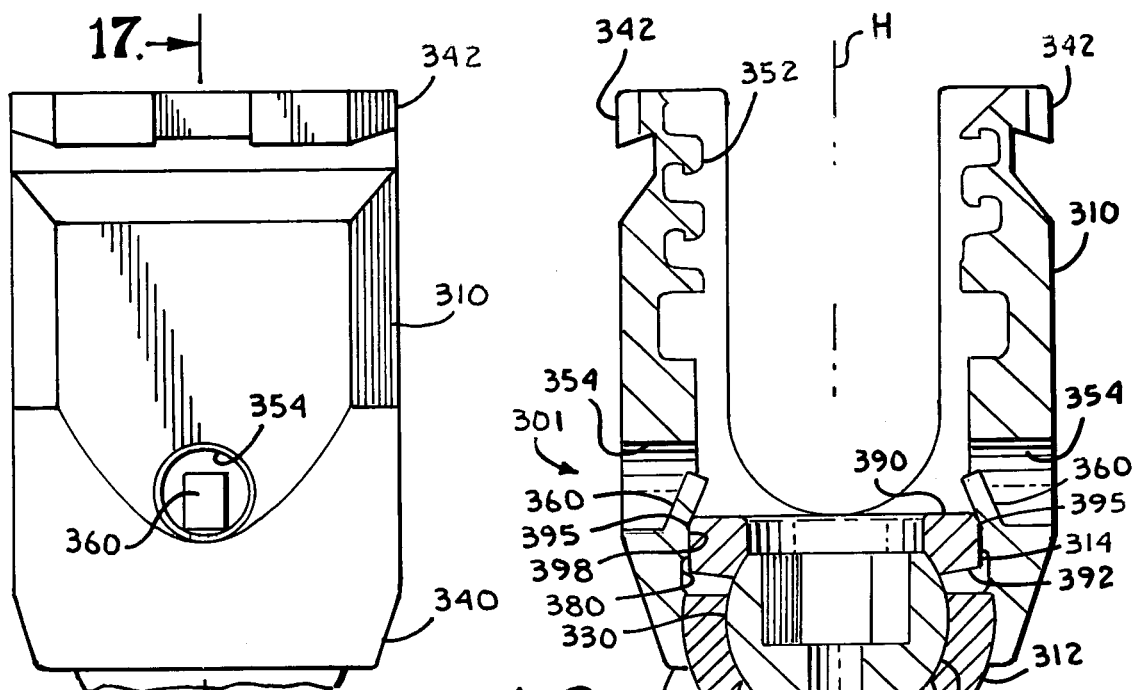
Fig. 16.
Fig. 17.
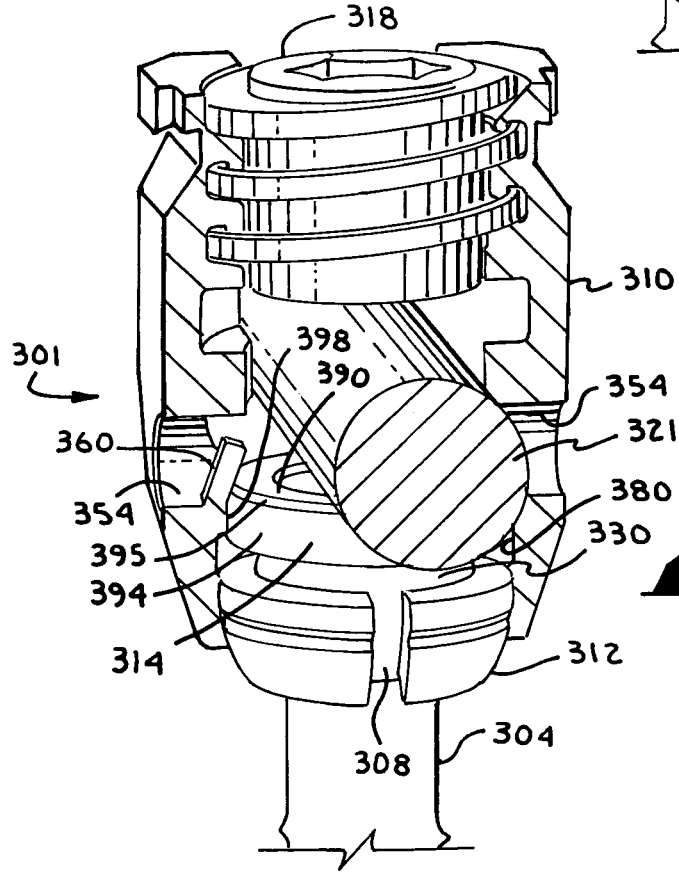
Fig. 18.

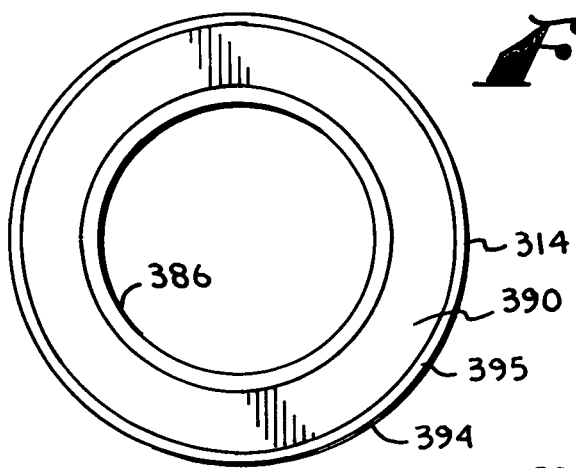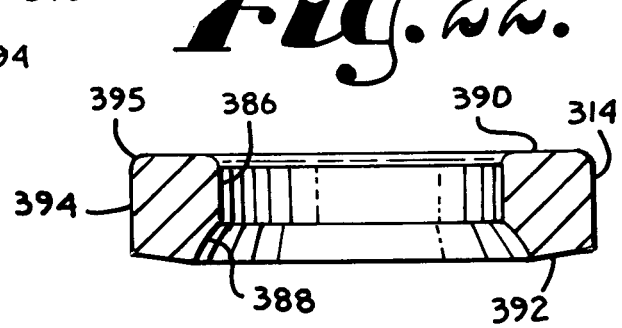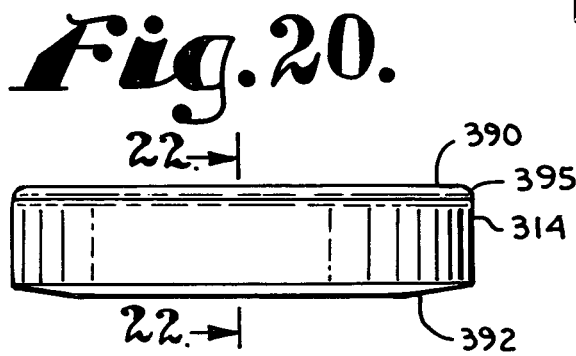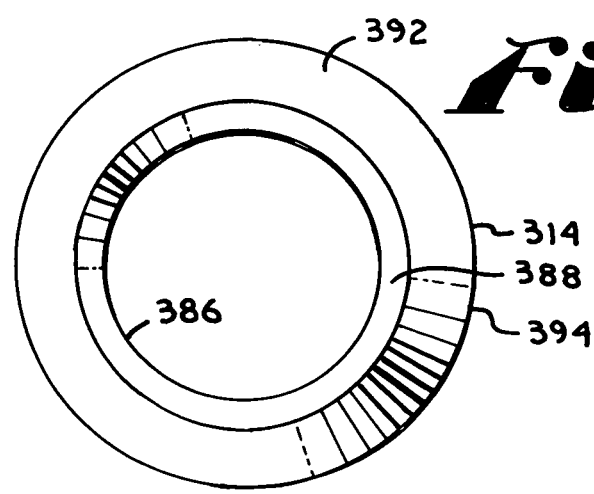

POLYAXIAL BONE SCREW WITH SPHERICAL CAPTURE, COMPRESSION INSERT AND ALIGNMENT AND RETENTION STRUCTURES

CROSS REFERENCE TO RELATED APPLICATIONS

This application is a continuation of U.S. patent Ser. No. 12/072,354, filed Feb. 26, 2008 that claimed the benefit of U.S. Provisional Application No. 60/905,472 filed Mar. 7, 2007, both of which is incorporated by reference herein. U.S. patent Ser. No. 12/072,354 was also a continuation-in-part of U.S. patent application Ser. No. 11/126,965 filed May 10, 2005 which is incorporated by reference herein. U.S. patent Ser. No. 12/072,354 was also a continuation-in-part of U.S. patent application Ser. No. 12/008,067 filed Jan. 8, 2008 that claimed the benefit of U.S. Provisional Application No. 60/897,723 filed Jan. 26, 2007, all of which are incorporated by reference herein. This application is also a continuation-in-part of U.S. patent application Ser. No. 12/924,260, now U.S. Pat. No. 8,403,962, filed Sep. 23, 2010 that was a continuation-in-part of U.S. patent application Ser. No. 11/385,957, filed Mar. 21, 2006, that was a continuation-in-part of U.S. patent application Ser. No. 11/178,854 filed Jul. 11, 2005, now U.S. Pat. No. 7,789,896, that claimed the benefit of U.S. Provisional Application No. 60/655,239 filed Feb. 22, 2005.

BACKGROUND OF THE INVENTION

The present invention is directed to polyaxial bone screws for use in bone surgery, particularly spinal surgery, and particularly to capture structures and inserts for such screws.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include open ends for receiving rods or portions of other structure.

A common mechanism for providing vertebral support is to implant bone screws into certain bones which then in turn support a longitudinal structure such as a rod, or are supported by such a rod. Bone screws of this type may have a fixed head or receiver relative to a shank thereof. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred.

Open-ended polyaxial bone screws allow rotation of the head or receiver about the shank until a desired rotational position of the head is achieved relative to the shank. Thereafter, a rod can be inserted into the head or receiver and eventually the receiver is locked or fixed in a particular position relative to the shank.

During the rod implantation process it is desirable to utilize bone screws or other bone anchors that have components that remain within the bone screw and further remain properly aligned during what is sometimes a very lengthy, difficult procedure. For example, some bone screws desirably include compression inserts or other parts that are designed to securely and fully engage surface portions of a rod or other longitudinal connecting member.

SUMMARY OF THE INVENTION

A polyaxial bone screw assembly according to the invention includes a shank having an upper portion and a body for fixation to a bone; a head or receiver defining an open channel; an articulation structure for retaining the shank upper portion within the receiver; and at least one compression insert. The articulation structure is disposed between the receiver and the shank upper portion and is slidingly mated to both the upper portion and the receiver, allowing for compound articulation of the shank with respect to the receiver. The receiver includes structure cooperating with the compression insert that retain such insert in a desired position and alignment within the receiver. Illustrated embodiments include spring tabs that project into the receiver cavity either upwardly or downwardly and into grooves or slots and/or flat surfaces formed in or on the insert.

OBJECTS AND ADVANTAGES OF THE INVENTION

Therefore, objects of the present invention include: providing an improved spinal implant assembly for implantation into vertebrae of a patient; providing such an assembly that includes an open longitudinal connecting member receiver, a shank pivotally connected to the rod receiving member, a rod or other longitudinal connecting member, and in some instances, an aligned pressure insert disposed between the shank and the rod; providing such an assembly that has a low profile after final installation; and providing such an assembly that is easy to use, especially adapted for the intended use thereof and wherein the implant assembly components are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 2 is an enlarged and partial side elevational view of the bone screw assembly of FIG. 1.

FIG. 3 is an enlarged and partial cross-sectional view taken along the line 3-3 of FIG. 2.

FIG. 4 is an enlarged and partial perspective view of the bone screw assembly of FIG. 1 with portions broken away to show the detail thereof.

FIG. 5 is an enlarged front elevational view of the compression insert of FIG. 1.

FIG. 6 is an enlarged side elevational view of the compression insert of FIG. 1.

FIG. 7 is a cross-sectional view taken along the line 7-7 of FIG. 5.

FIG. 8 is an enlarged front elevational view of the retainer of FIG. 1.

FIG. 9 is an enlarged rear elevational view of the retainer of FIG. 1.

FIG. 10 is an enlarged front elevational view, similar to FIG. 8 with portions broken away to show the detail thereof.

FIG. 12 is an enlarged and partial side elevational view of the bone screw assembly of FIG. 11.

FIG. 13 is an enlarged and partial cross-sectional view taken along the line 13-13 of FIG. 12.

FIG. 14 is an enlarged and partial perspective view of the bone screw assembly of FIG. 11 with portions broken away to show the detail thereof.

FIG. 16 is an enlarged and partial side elevational view of the bone screw assembly of FIG. 15.

FIG. 17 is an enlarged and partial cross-sectional view taken along the line 17-17 of FIG. 16.

FIG. 18 is an enlarged and partial perspective view of the bone screw assembly of FIG. 15 with portions broken away to show the detail thereof.

FIG. 19 is an enlarged top plan view of the compression insert of FIG. 15.

FIG. 20 is an enlarged front elevational view of the compression insert of FIG. 15.

FIG. 21 is an enlarged bottom plan view of the compression insert of FIG. 15.

FIG. 22 is a cross-sectional view taken along the line 22-22 of FIG. 20.

DETAILED DESCRIPTION OF THE INVENTION

Figure 1:
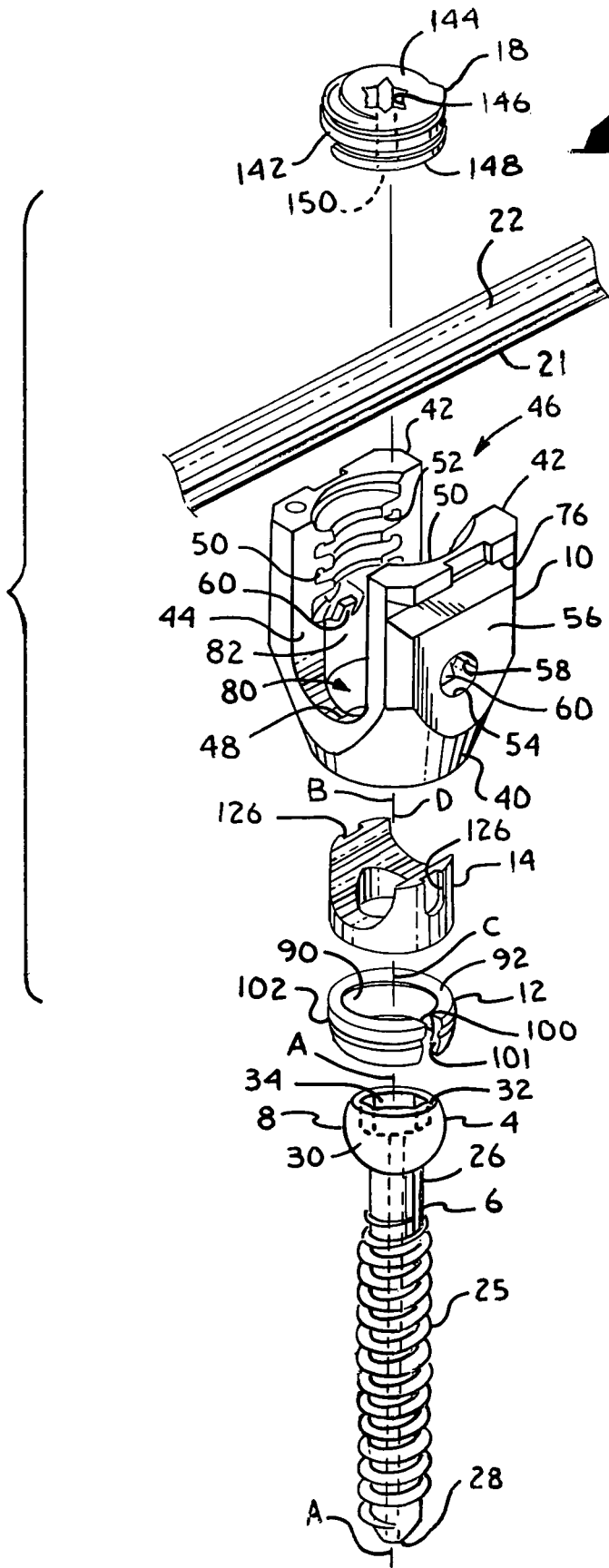
FIG. 1 is an enlarged exploded perspective view of a bone screw assembly according to the invention including a shank, a retainer, a compression insert and a receiver and shown with a cooperating longitudinal connecting member and a cooperating closure top.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

With reference to FIGS. 1-10, the reference numeral 1 generally designates a polyaxial bone screw assembly according to the present invention. The assembly 1 includes a shank 4 that further includes a body 6 integral with an upper portion or capture structure 8; a head or receiver 10; a retainer 12 illustrated as an open collar-like retaining and articulating structure; and a compression insert 14. The shank 4, head or receiver 10, retainer 12 and insert 14 are assembled prior to implantation of the shank body 6 into a vertebra 15.

FIG. 1 also shows a closure structure or top 18 for capturing a longitudinal connecting member within the head or receiver 10, such as a rod 21 having an outer cylindrical surface 22. Upon installation, which will be described in detail below, the closure top 18 presses against the rod 21 that in turn presses against the insert 14 that presses against the shank upper portion 8 which presses the retainer 12 into fixed frictional contact with the receiver 10, so as to fix the rod 21 relative to the bone screw 1 and thus to adjacent vertebrae. The receiver 10 and shank 4 cooperate in such a manner that the receiver 10 and shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other.

The bone screw shank 4, best illustrated in FIGS. 1 and 3, is elongate, with the shank body 6 having a helically wound bone implantable thread 25 extending from near a neck 26 located adjacent to the upper portion 8 to near a tip 28 of the body 6 and extending radially outwardly therefrom. During use, the body 6 utilizing the thread 25 for gripping and advancement is implanted into a vertebra (not shown) leading with the tip 28 and driven down into the vertebra with an installation or driving tool (not shown), so as to be implanted in the vertebra to near the neck 26. The shank 4 has an elongate axis of rotation generally identified by the reference letter A.

The neck 26 extends axially upwardly from the shank body 6. Further extending axially from the neck 26 is the shank upper portion or capture structure 8 that provides a connective or capture apparatus disposed at a distance from the thread 25 and thus at a distance from the vertebra (not shown) when the body 6 is implanted in such vertebra. The shank upper portion 8 is configured for connecting the shank 4 to the receiver 10 and capturing the shank 4 in the receiver 10. The shank upper portion 8 has an outer, convex and substantially spherical surface 30 that extends outwardly and upwardly from the neck 26 and terminates at a top 32. The illustrated top 32 is substantially planar and disposed perpendicular to the axis A. The spherical surface 30 has an outer radius configured for sliding cooperation and ultimate frictional mating with a concave surface of the retainer 12 that has a substantially similar radius. The spherical surface 30 is smooth, but it is foreseen that such surface may include a roughened or textured surface or surface finish, or may be scored, knurled, or the like, for enhancing frictional engagement with the retainer 12. A counter sunk drive feature 34 is formed in the top 32 (shown as a hexagonal aperture). In operation, a driving tool (not shown) engages the feature 34 for driving the shank body 6 into bone. The drive feature 34 may take a variety of tool-engaging forms and may include one or more apertures or imprints of various shapes, such as a pair of spaced apart apertures or a multi-lobular aperture, such as those sold under the trademark TORX or the like. It is foreseen that in some embodiments, the bone screw shank upper portion may have an external tool engagement structure.

The illustrated shank 4 is cannulated, having a small central bore 35 extending an entire length of the shank 4 along the axis A, coaxial with the threaded body 6. The bore 35 has a first circular opening at the shank tip 28 and a second circular opening at the drive feature 34. The bore 35 provides a passage through the shank 4 interior for a length of wire (not shown) inserted into a vertebra (not shown) prior to the insertion of the shank body 6, the wire providing a guide for insertion of the shank body 6 into the vertebra.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With reference to FIGS. 1-4, the receiver 10 has a generally U-shaped appearance with a discontinuous partially cylindrical and partially spherical inner profile and a partially curved and partially faceted outer profile. The receiver has an axis of rotation B that is shown in FIG. 1 as being aligned with and the same as the axis of rotation A of the shank 4, such orientation being desirable during assembly of the receiver 10 with the shank 4, the retainer 12 and the insert 14. After the receiver 10 is pivotally attached to the shank 4, and the assembly 1 is implanted in a vertebra (not shown), the axis B is typically disposed at an angle with respect to the axis A.

The receiver 10 includes a base 40 integral with a pair of opposed upstanding arms 42 forming a cradle and defining a U-shaped channel 44 between the arms 42 with an upper opening 46 and a lower seat 48, the channel 44 having a width for receiving the rod 21, for operably snugly receiving the rod 21 between the arms 42. Each of the arms 42 has an interior surface 50 that defines the inner cylindrical profile and includes a partial helically wound guide and advancement structure 52. In the illustrated embodiment, the guide and advancement structure 52 is a partial helically wound interlocking flangeform configured to mate under rotation with a similar structure on the closure structure 18, as described more fully below. However, it is foreseen that the guide and advancement structure 52 could alternatively be a square-shaped thread, a buttress thread, a reverse angle thread or other thread like or non-thread like helically wound discontinuous advancement structure for operably guiding under rotation and advancing the closure structure 18 downward between the arms 42, as well as eventual torquing when the closure structure 18 abuts against the rod 21.

An opposed pair of tool receiving and engaging apertures 54 are formed on outer surfaces 56 of the arms 42. A pair of substantially cylindrical inner surfaces 58 define the apertures 54, with a portion of each of the apertures 54 extending through the arms 42 as best illustrated in FIG. 2. With particular reference to FIGS. 3 and 4, a pair of tabs 60, each having a lower end or body portion 62 integral with a respective arm 42 at a lower portion of one of the cylindrical surfaces 58, and an upper end 64 extending upwardly and inwardly from the respective lower body portion 62, the tab 60 generally directed towards the guide and advancement structure 52 of the respective arm 42 and also toward the axis B. As shown in FIGS. 1, 3 and 4, an operational orientation of each of the tabs 60 is angled toward the axis B with an inner surface 68 or edge 69 of the upper end 64 in sliding engagement with a slot in the cooperating insert 14 as will be described in greater detail below. The tabs 60 are typically initially disposed parallel to the axis B and then a tool (not shown) is inserted into the aperture 54 from the outside surface 56 and engages and pushes a surface 66 of the tab 60 and bends the tab 60 inwardly in a direction toward the axis B until the tab 60 is at the illustrated desired angular position. Such bending of the tabs 60 may be performed either prior to or after assembly of the receiver 10 with the insert 14, the shank 4 and the retainer 12. It is also foreseen that the tabs 60 may be machined or otherwise pre-fabricated to be angled or directed toward the axis B as is shown in the drawing figures. The illustrated tabs 60 are resilient, having a spring-like nature. Thus, when operatively cooperating with the insert 14, the tabs 60 bias against the insert 14, holding such insert in a desired position and yet the tabs 60 are flexible enough to allow a user to make desired adjustments of the position of the insert 14 within the receiver 10.

Each of the illustrated receiver arms 42 also includes a V-shaped or undercut tool engagement groove 76, formed on outer surfaces thereof which may be used for holding the receiver 10 with a holding tool (not shown) having projections that are received within the grooves 76 during implantation of the shank body 6 and/or during subsequent installation of the rod 21 or other longitudinal connecting member and the closure structure 18. It is foreseen that tool receiving grooves or apertures may be configured in a variety of shapes and sizes and be disposed at other locations on the receiver arms 42.

Communicating with the U-shaped channel 44 of the receiver 10 is a chamber or cavity 80 defined in part by a substantially cylindrical upper portion 82 and by a lower inner substantially spherical seating surface 84 of the base 40. The upper portion 82 is located below the guide and advancement structures 52 and may include one or more cylindrical surfaces for sliding cooperation with an insert or inserts. As illustrated in FIG. 3, the cylindrical upper portion 82 may include a lower section or portion 85 having a larger diameter than a remainder of the portion 82, the portion 85 located adjacent to the spherical seat 84 and providing clearance for movement of the retainer 12, including an expanding or spreading movement thereof during attachment with the shank upper portion 8 and for swiveling the retainer 12 to a desired orientation after assembly of the bone screw 1. The apertures 54 and the tabs 60 communicate with the cylindrical upper portion 82. The seating surface 84 is near or adjacent to the cylindrical portion 82. The seating surface 84 is sized and shaped for slidable mating and eventual frictional engagement with the retainer 12, as described more fully below. The cavity 80 opens into the U-shaped channel 44 and also to a lower neck 86 defining a bore or circular opening that communicates with a lower exterior 88 of the base 40. The circular neck 86 is coaxially aligned with the rotational axis B of the receiver 10. The neck 86 is sized and shaped to be smaller than an outer radial dimension of the open, uncompressed retainer 12, as will be discussed further below, so as to form a restriction at the location of the neck relative to the retainer 12, to prevent the uncompressed retainer 12 from passing from the cavity 80 and out to the lower exterior 88 of the receiver 10 when the retainer 12 is seated and loaded.

With reference to FIGS. 1, 3, 4 and 8-10, the partially spherical and discontinuous or open retainer 12 that both retains and articulates is used to hold the spherically surfaced 30 upper portion 8 of the shank 4 within the receiver 10 and is also independently slidably and pivotally engageable with both the shank upper portion 8 at the surface 30 and the receiver 10 at the seating surface 84. The retainer 12 has an operational central axis C that may be the same or different from the axis A associated with the shank 4, or the axis B associated with the receiver 10 when the shank upper portion 8 and the retainer 12 are installed within the receiver 10. The retainer 12 has a central channel or through bore substantially defined by a discontinuous inner partially spherical surface 90. The surface 90 extends from a substantially planar annular top 92 to an inner neck 94 disposed near a substantially planar annular bottom surface 96. An inner chamfer 98 runs between the neck 94 and the bottom surface 96. The inner spherical surface 90 has a radius sized and shaped to cooperate with a radius of the substantially spherical surface 30 of the shank upper portion 8 such that the surface 90 slidingly and pivotally mates with the spherical surface 30. The surface 90 may include a roughening or surface finish to aid in frictional contact between the surface 90 and the surface 30, once a desired angle of articulation of the shank 4 with respect to the retainer 12 and also with respect to the receiver 10 is reached.

The resilient retainer 12 includes first and second end surfaces, 100 and 101 disposed in spaced relation to one another and a discontinuous outer partially spherically shaped surface 102. Both end surfaces 100 and 101 are disposed substantially perpendicular to the top surface 92 and the bottom surface 96. A width of the space between the surfaces 100 and 101 is determined to provide adequate space for the retainer 12 to be pinched, with the surfaces 100 and 101 compressed toward one another to an almost touching or touching configuration, to an extent that the compressed retainer 12 is up or bottom loadable into the receiver cavity 80 being received within the lower neck 86 opening of the receiver 10 while mounted on the neck 26 of the bone screw shank body 6. After passing through the bore defined by the lower neck 86 of the receiver 10 simultaneously with the shank upper portion 8, the retainer 12 expands or springs back to an original uncompressed, rounded or collar-like configuration of FIG. 1 once in the cavity 80. The retainer 12 is then expanded about the shank upper portion spherical surface 30 as will be described in greater detail below. Then, once the resilient structure 12 returns to an original form, but now surrounding the spherical structure 30, the engaged structures 8 and 12 are movable together within the cavity 80 at the spherical seat 84 to a variety of positions in which the surface 102 of the retainer 12 is in slidable mating engagement with the seating surface 84 of the receiver 10.

Figure 25:
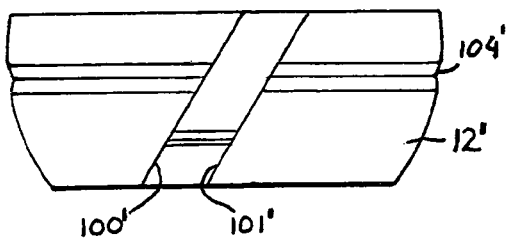
FIG. 25 is an enlarged rear elevational view of an alternative embodiment of the retainer of FIG. 1 shown in FIG. 9.

The illustrated embodiment of the retainer 12 shows the surfaces 100 and 101 as substantially parallel and vertical, however, in other embodiments according to the invention, such as the retainer 12' shown in FIG. 25, opposing surfaces 100' and 101' are oriented obliquely or at a slight angle with respect to top and bottom surfaces thereof, advantageously allowing for the surfaces 100' and 101' to slide and ride up upon one another during assembly with the other components of the assembly 1, allowing for greater compression of the retainer 12' without increasing the space between the surfaces 100' and 101' when the retainer 12' is in an uncompressed state. Depending upon the amount of compression desired during loading of the retainer 12' into the receiver 10, the oblique angle may be modified. The retainer 12' is otherwise identical or substantially similar to the retainer 12 in form and function. Furthermore, the illustrated embodiment 12 and 12' include an outer groove 104 and 104', respectively, that may be needed in some instances for clearance within the receiver 10 when the retainer 12 or 12' is expanded about the spherical surface 30 of the shank upper portion 8. Also, other embodiments according to the invention, particularly smaller bone screw assemblies, may include retainers small enough to top load into the receiver channel upper opening 46, rather than loading through the receiver neck 86.

With reference to FIGS. 1, 3 and 4, the compression member or insert 14 is sized and shaped to be received by and uploaded into the receiver 10 at the lower neck 86. In operation, the insert 14 is disposed between the rod 21 and the upper portion 8 of the bone screw 4 as illustrated for example in FIGS. 3 and 4. When the closure structure 18 presses upon the rod 21, the rod 21 operatively presses upon the insert 14 that in turn presses upon the shank upper portion 8 that in turn presses against the retainer 12 that in turn presses against the seating surface 84 of the receiver 10, resulting in ultimate frictional engagement and locking of the angular position of the bone screw shank 4 with respect to the receiver 10. The compression insert 14 has an operational central axis D that is the same as the central axis B of the receiver 10.

With particular reference to FIGS. 5-7, the compression insert 14 has a central channel or through bore substantially defined by a an inner cylindrical surface 110 and an inner partially spherical surface 112, both having the central axis D. The compression insert 14 through bore is sized and shaped to receive a driving tool (not shown) therethrough that engages the shank drive feature 34 when the shank body 6 is driven into bone. The surface 112 is sized and shaped to cooperate with the spherical surface 30 of the shank upper portion 8 such that the surface 112 slidingly and pivotally mates with the spherical surface 30. The surface 112 may include a roughening or surface finish to aid in frictional contact between the surface 112 and the surface 30, once a desired angle of articulation of the shank 4 with respect to the retainer 12 and the receiver 10 is reached.

The compression insert 14 also includes a pair of arms 114 with a U-shaped surface or saddle 116 formed therebetween. The saddle 116 defines a U-shaped channel that communicates with the bore defined by the cylindrical surface 110 and the spherical surface 112. The curved surface or saddle 116 is sized and shaped to closely receive the cylindrical rod 21. With reference to the axis D, the saddle 116 extends from top surfaces 118 of the arms to a curved lower seat 120 near a bottom surface 122 of the insert 114. In operation, the lower seat 129 (as well as a substantial portion of a remainder of the saddle 116) frictionally engages the surface 22 of the rod 21.

A base having a cylindrical surface 124 is disposed between the saddle 116 and the bottom surface 122. The cylindrical surface 124 also extends about the arms 114. Formed in the surface 124 and located centrally with respect to each arm 114 is a shallow groove 126. Each groove 126 is U-shaped and runs from the respective top surface 118 to a curved bottom 128 located approximately centrally between the top surface 118 and the bottom surface 122. The grooves 126 are sized and shaped to cooperate with the tabs 60 of the receiver 10 as will be described in greater detail below. Thus, although the grooves 126 may be of any shape, the grooves 126 preferably are elongate, running parallel to the axis D and have a width that receives the respective tab 60 within such groove. The bottom surface 122 includes a substantially planar and annular central portion 130 disposed perpendicular to the axis D. The bottom portion 130 extends about the bore defined by the inner spherical surface 112. The bottom surface 122 further includes an outer planar and annular surface portion 132 disposed at an angle with respect to the surface portion 130. The surface portion 132 angles upwardly (toward the top surfaces 118) and outwardly (away from the axis D) from the surface 130. As shown in FIG. 3, the surface portion 132 provides clearance for articulated movement of the retainer 12 and the bone screw shank 4.

The compression or pressure insert 14 ultimately seats on the shank upper portion 8 and is disposed substantially in the upper cylindrical portion 82 of the cavity 80, with the tabs 60 holding the insert 14 in desired alignment with respect to the rod 21 as will be described in greater detail below. In operation, the insert 14 extends at least partially in the channel 44 such that the saddle 116 surface substantially contacts and engages the outer surface 22 of the rod 21 when such rod is placed in the receiver 10 and the closure structure or top 18 is tightened therein.

With reference to FIGS. 1 and 4, the closure structure or closure top 18 can be any of a variety of different types of closure structures for use in conjunction with the present invention with suitable mating structure on the upstanding arms 42. In the embodiment shown, the closure top 18 is rotatably received between the spaced arms 42, but could be a slide-in closure structure. The illustrated closure structure 18 is substantially cylindrical and includes an outer helically wound guide and advancement structure 142 in the form of a flange form that operably joins with the guide and advancement structure 52 disposed on the arms 42 of the receiver 10. The flange form utilized in accordance with the present invention may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 18 downward between the arms 42 and having such a nature as to resist splaying of the arms 42 when the closure structure 18 is advanced into the U-shaped channel 44. The illustrated closure structure 18 also includes a top surface 144 with an internal drive 146 in the form of an aperture that may be a hex drive, or as illustrated, a star-shaped internal drive, for example, sold under the trademark TORX or other internal drives such as slotted, tri-wing, spanner, two or more apertures of various shapes, and the like. A driving tool (not shown) sized and shaped for engagement with the internal drive 146 is used for both rotatable engagement and, if needed, disengagement of the closure 18 from the receiver arms 42. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A bottom surface 148 of the closure may be planar or include a point, points, a rim or roughening for engagement with the surface 22 of the rod 21. The illustrated closure top 18 further includes a cannulation through bore 150 extending along a central axis thereof and through the top surface 144 and the bottom surface 148. Such a through bore provides a passage through the closure 18 interior for a length of wire (not shown) inserted therein to provide a guide for insertion of the closure top into the receiver arms 42.

Prior to the polyaxial bone screw assembly 1 being placed in use according to the invention the tabs 60 of the receiver 10 are preferably bent inwardly toward the axis B as shown in FIGS. 1, 2 and 4. This is accomplished by inserting an elongate tool (not shown) into each of the tooling apertures 54 and pressing the respective tab 60 inwardly toward the axis B until the tab end 64 is disposed at least partially within the upper cylindrical portion 82 of the cavity 80. It is noted that alternatively, in some embodiments according to the invention, the tabs 60 are bent inwardly toward the axis B after the pressure insert 14 is located in the cylindrical portion 82 of the cavity 80. For example, if the insert 14 is top loaded through the opening 46 of the receiver 10, it may be desirable to first load the insert 14 into the receiver, align the grooves 126 with the tabs 60 and then press the tabs 60 until such tabs come into frictional engagement with surfaces of the receiver 14 disposed within the shallow grooves 126.

Also prior to the polyaxial bone screw assembly 1 being placed in use according to the invention, the retainer 12 is first inserted about the neck 26 of the shank body 6 by inserting the shank tip 28 into the retainer 12 through bore defined by the inner surface 90 and feeding the shank body 6 therethrough until the retainer 12 is located at the neck 26. Alternatively, in certain embodiments, the retainer 12 is placed near the neck 26 and the end surfaces 100 and 101 are pulled away from one another and pressed against and about the neck 26 until the surfaces 100 and 101 expand around the neck 26 and then spring back into an original or first position with the inner surface 90 disposed adjacent to the neck 26 and the top surface 92 facing toward the spherical surface 30 of the shank upper portion 8.

In the illustrated embodiment, prior to inserting the shank 4 and connected retainer 12 into the receiver 10, the compression insert 14 is up or bottom loaded into the receiver 10 through the lower neck 86 with the saddle 116 facing the neck 86 and the arms 114 aligned with the tabs 60. The insert 14 is then moved upwardly through the lower seat 84 of the receiver 10 and into the cylindrical portion 82 of the cavity 80. As the insert 14 is moved upwardly into the cylindrical portion 82, each of the tabs 60 are received in a groove 126. The tabs 60 press against the insert 14 at the grooves 126, allowing for some upward and downward adjustment of the insert 14. However, rotation of the insert 14 about the axis B is prohibited by the tabs 60 abutting against surfaces forming the grooves 126. Surfaces defining the lower curved portion 128 of the grooves 126 also prohibit the tabs 60 from sliding along the outer cylindrical surface 124 of the insert 14, thus resisting upward movement of the insert 14 out of the receiver 10.

In certain embodiments, it may be desirable to place the compression insert 14 on the shank upper portion 8 with the spherical surface 112 seated on the surface 30 of the shank upper portion 8 and then upload the insert 14 simultaneously with the shank upper portion 8 and the retainer 12. The upper portion 8 and the connected retainer 12 are simultaneously up or bottom-loaded into the receiver cavity 80 by inserting the upper portion 8 through the lower neck 86 and into the cavity 80 lower seat portion 84 and manually compressing the retainer 12 by pinching the surfaces 100 and 101 toward one another and inserting the neck 26 and the compressed retainer 12 into the bore formed by the lower neck 86 of the receiver 10. After the retainer 12 moves beyond the neck 86, the compressive force is removed and the retainer 12 resiliently springs back and returns to the original ring-like or collar-like orientation, capturing the shank upper portion 8 within the receiver 10. Then, the shank body 6 is pulled downwardly away from the base 40 of the receiver 10, forcing the retainer 12 to temporarily expand as the retainer 12 moves along the spherical surface 30 of the shank upper portion 8 with the end surfaces 100 and 101 moving away from one another. Such an expansion of the retainer 12 allows the spherical surface 30 to slide or snap into the retainer 12 with the spherical surfaces 30 and 90 becoming aligned and the shank upper portion 8 ultimately in sliding cooperation with the inner surface 90 of the retainer 12. The retainer 12 thus resiliently returns to the original ring-link orientation, with the spherical surface 90 capturing the shank upper portion 8 at the spherical surface 30, but allowing for pivotal movement or articulation of the shank upper portion 8 with respect to the retainer 12. Once the retainer 12 returns to the original orientation, both the connected structures 8 and 12 drop down to a seated position at the spherical surface 84 of the receiver 10, with the retainer 12 being independently slidable with respect to both the shank upper portion 8 and the receiver 10, forming a multi- or compound articulation or joint between the shank 4 and the receiver 10. The compression insert 14 may then be pressed downwardly and into full contact with the surface 30.

The retainer 12 and the attached shank upper portion 8 may then be manipulated into a substantially coaxial position with the insert 14 in readiness for bone implantation. The assembly 1 is typically screwed into a bone, such as a vertebra (not shown), by rotation of the shank 4 using a driving tool (not shown) that operably drives and rotates the shank 4 by engagement thereof with the drive feature 34.

Typically, the receiver 10, the compression or pressure insert 14, and the retainer 12 are assembled on the shank 4 before inserting the shank body 6 into a vertebra. However, in certain circumstances, such as when a small bone screw is utilized and the retainer is top loadable, the shank body 6 can be first partially implanted with the shank upper portion 8 extending proud to allow assembly with the receiver 10, followed by assembly with a top loaded retainer 12 and a top loaded compression insert 14. Then the shank body 6 can be further driven into the vertebra.

The vertebra (not shown) may be pre-drilled to minimize stressing the bone and have a guide wire (not shown) inserted to provide a guide for the placement and angle of the shank 4 with respect to the vertebra. A further tap hole may be made using a tap with the guide wire as a guide. Then, the bone screw assembly 1 or the solitary shank 4, is threaded onto the guide wire utilizing the cannulation bore 35 by first threading the wire into the opening at the bottom 28 and then out of the top opening at the drive feature 34. The shank 4 is then driven into the vertebra using the wire as a placement guide. It is foreseen that the bone screw assemblies 1, the rod 21 (also having a central lumen in some embodiments) and the closure top 18 can be inserted in a percutaneous or minimally invasive surgical manner, utilizing guide wires.

With reference to FIG. 4, the rod 21 is eventually positioned in an open or percutaneous manner in cooperation with the at least two bone screw assemblies 1. Alignment of the rod surface 22 with the saddle 116 of the insert 14 is initially provided and then maintained by pressure placed at the insert grooves 126 by the tabs 60. A closure structure 18 is then inserted into and advanced between the arms 42 of each of the bone screw assemblies 1. The closure structure 18 is rotated, using a tool engaged with the inner drive 146 until a selected pressure is reached at which point the rod 21 engages the saddle 116 and the rod is urged toward, but not in contact with the lower seat 48 of the receiver 10 that defines the U-shaped channel 44. For example, about 80 to about 120 inch pounds pressure may be required for fixing each bone screw shank 7 with respect to the receiver 10.

As each closure structure 18 rotates and moves downwardly into the respective receiver 10, the bottom surface 148 presses against the rod surface 22, biasing the rod into engagement with the compression insert 14 that operably produces a frictional engagement between the insert surface 112 and the shank surface 30 and also urges the shank upper portion 8 toward the retainer 12 and, in turn, the structure 12 in a direction toward the base 40 of the receiver 10, so as to frictionally seat the spherical surface 30 against the inner spherical surface 90 of the retainer 12 and the outer spherical surface 102 of the retainer 12 against the internal spherical seating surface 84 of the receiver 10, also fixing the shank 4 and the retainer 12 in a selected, rigid position relative to the receiver 10. At this time it is also possible for the retainer 12 to expand somewhat for an even tighter fit in the receiver cavity lower seat 84.

If removal of the rod 21 from any of the bone screw assemblies 1 is necessary, or if it is desired to release the rod 21 at a particular location, disassembly is accomplished by using the driving tool (not shown) that mates with the internal drive 146 on the closure structure 18 to rotate and remove the closure structure 18 from the cooperating receiver 10. Disassembly is then accomplished in reverse order to the procedure described previously herein for assembly.

With reference to FIGS. 11-14, an alternative bone screw assembly of the invention, generally 201 includes a shank 204 that further includes a body 206 integral with an upper portion or capture structure 208; a head or receiver 210; a retainer 212 illustrated as an open collar-like retaining and articulating structure; and a compression insert 214. The shank 204, the retainer 212 and the insert 214 are identical or substantially similar to the respective shank 4, retainer 12 and insert 14 previously described herein. The assembly 201 also cooperates with the rod 221 and a closure top 218 that are the same or similar to the respective rod 21 and closure top 18 previously described herein. The receiver 210 is substantially similar to the receiver 10 with the exception of the orientation of spring tabs 260 that are otherwise substantially similar to the tabs 60 previously described herein with respect to the assembly 1. Similar to the previous discussion with respect to the assembly 1, the tabs 260 of the receiver 210, like the tabs 60 of the receiver 10, press against shallow grooves formed on an outside surface of the insert 214, keeping a saddle or curved surface of the insert 212 in a desired alignment to receive and ultimately frictionally engage the rod 221 along a substantial surface of the saddle. The insert may also have a flat outer surface instead of shallow grooves.

Because the illustrated assembly 201 only differs from the assembly 1 with respect to the tabs 260 of the receiver 210, only relevant portions of the receiver 210 will be described in greater detail here: The receiver 210 includes a base 240 integral with a pair of opposed upstanding arms 242 forming a cradle and defining a U-shaped channel 244 between the arms 242 with an upper opening 246 and a lower seat 248, the channel 244 having a width for receiving the rod 221, for operably receiving the rod 221 between the arms 242. Each of the arms 242 has an interior surface 250 that defines the inner cylindrical profile disposed about a central axis G and includes a partial helically wound guide and advancement structure 252. In the illustrated embodiment, the guide and advancement structure 252 is a partial helically wound interlocking flangeform configured to mate under rotation with a similar structure on the closure structure 218. However, it is foreseen that the guide and advancement structure 252 could alternatively be a square-shaped thread, a buttress thread, a reverse angle thread or other thread like or non-thread like helically wound discontinuous advancement structure for operably guiding under rotation and advancing the closure structure 218 downward between the arms 242, as well as eventual torquing when the closure structure 218 abuts against the rod 221.

Figure 11:
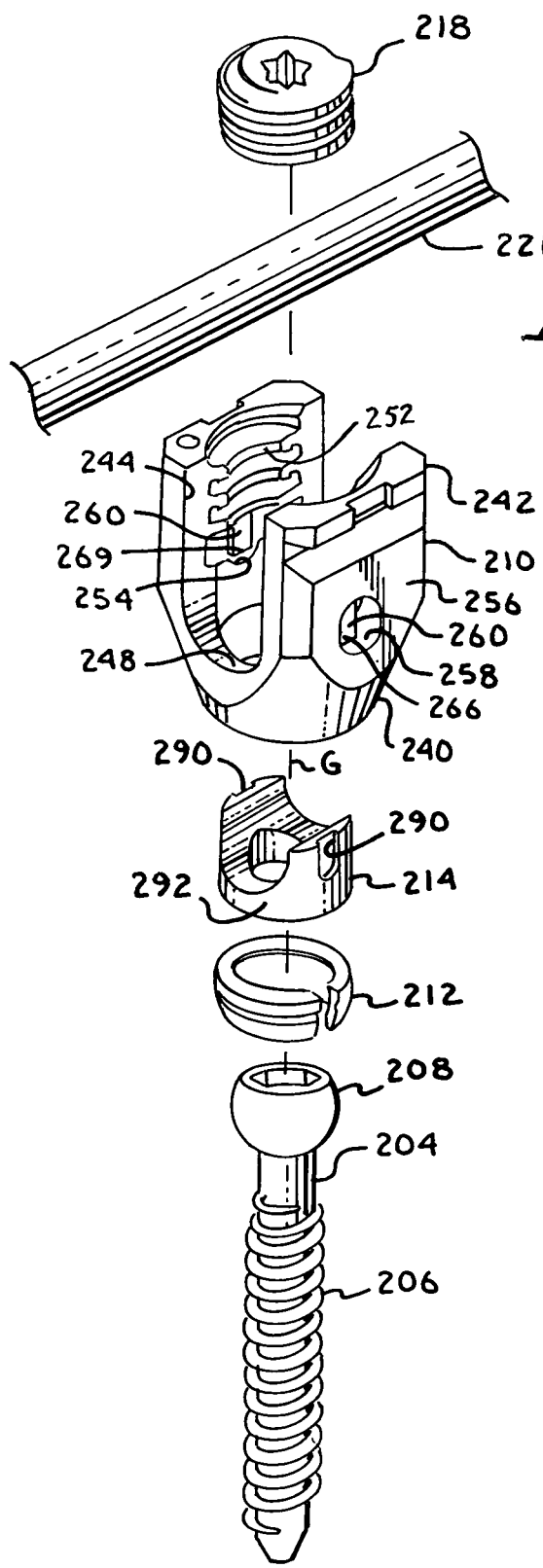
FIG. 11 is an enlarged exploded perspective view of a second embodiment of a bone screw assembly according to the invention including a shank, a retainer, a compression insert and a receiver and shown with a cooperating longitudinal connecting member and a cooperating closure top.
Figure 15:
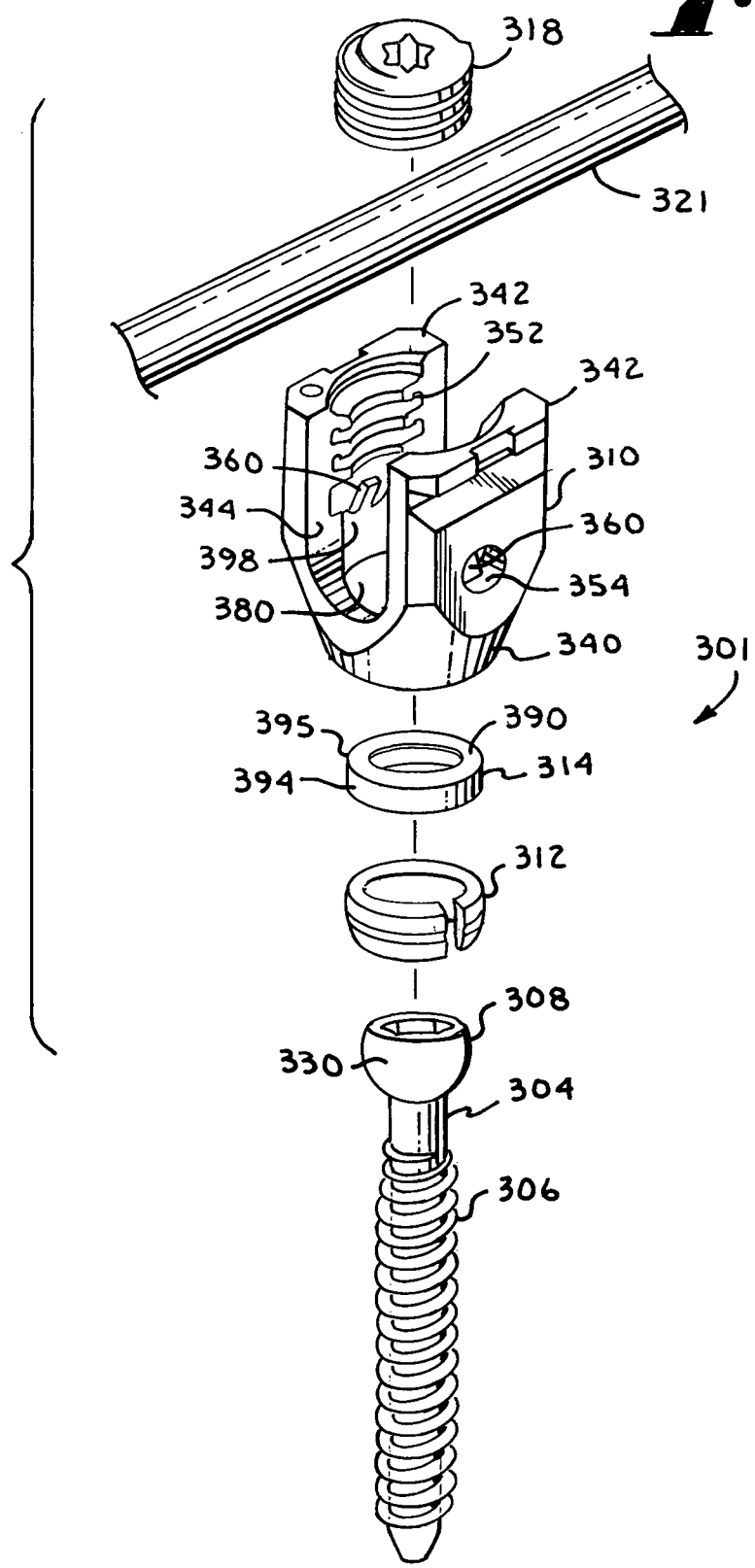
FIG. 15 is an enlarged exploded perspective view of a third embodiment of a bone screw assembly according to the invention including a shank, a retainer, a compression insert and a receiver and shown with a cooperating longitudinal connecting member and a cooperating closure top.

An opposed pair of tool receiving and engaging apertures 254 are formed on outer surfaces 256 of the arms 242. A pair of substantially cylindrical inner surfaces 258 define the apertures 254, with a portion of each of the apertures 254 extending through the arms 242 as best illustrated in FIG. 12. With particular reference to FIGS. 11, 13 and 14, the pair of tabs 260, each having an upper end or body portion 262 integral with a respective arm 242 at an upper portion of one of the cylindrical surfaces 258, and a lower end 264 extending downwardly and eventually inwardly from the respective upper body portion 262 toward the central axis G of the receiver 210. As shown in FIG. 14, an operational orientation of each of the tabs 260 is angled toward the central axis G of the receiver with an inner surface 268 or edge 269 of the lower end 264 in sliding engagement with a slot 290 in the cooperating insert 214. As illustrated in FIGS. 11 and 13, the tabs 260 are typically initially disposed parallel to the central axis of the receiver 210. In the illustrated embodiment, the pressure insert 214, retainer 212 and bone screw shank 204 are first bottom loaded (or may be top loaded) into the receiver 210 in a manner as previously described herein with respect to the assembly 1 and then a tool (not shown) is inserted into each aperture 254 from the outside surface 256 and engages and pushes a surface 266 of the tab 260 and bends the tab 260 inwardly in a direction toward the receiver central axis G until the tab 260 is at the illustrated desired angular position. Such bending of the tabs 260 may also be performed prior to assembly of the receiver 210 with the insert 214, shank 204 and retainer 212. In such an arrangement, the insert 214 may be uploaded or downloaded into the receiver 210 with the saddle portion thereof in alignment with the tabs 260. After the insert 214 is in a desired axial position, the insert 214 is rotated about the axis G with the tabs 260 being manipulated to press against the surface 292. The insert 214 is rotated about the central axis G until the tabs 260 snap into the grooves or depressions 290 (or engage flat surfaces).

It is foreseen that in another embodiment according to the invention, the insert 214 is sized and shaped for top loading into the opening 246 of the receiver 210 and the tabs 260 are bent inwardly toward the axis G prior to assembly of the receiver 210 with the insert 214 and the other bone screw components. During assembly, after the insert 214 is lowered into the receiver 210 and moved past the guide and advancement structure 252, the outer surface 292 presses against the tabs 260, moving the tabs 260 outwardly and away from one another. Then, when the edges 269 of the tabs 260 come into contact with the surface of the grooves 290, the resilient tabs 260 snap into such grooves, maintaining alignment of the insert 214 and resisting any rotational movement of the insert 214 as the insert 214 is lowered into place over the upper portion 208 of the bone screw shank 204.

It is also foreseen that the tabs 260 may be machined or otherwise pre-fabricated to be angled or directed toward the receiver central axis G. As indicated above, the illustrated tabs 260 are resilient, having a spring-like nature. Thus, when operatively cooperating with the insert 214, the tabs 260 bias against the insert 214, holding such insert in a desired position. However, the tabs 260 are flexible enough to allow a user to make desired upward and downward adjustments of the position of the insert 214 within the receiver 210 with respect to the axis G.

With reference to FIGS. 15-21, a third embodiment of a bone screw assembly of the invention, generally 301 includes a shank 304 that further includes a body 306 integral with an upper portion or capture structure 308; a head or receiver 310; a retainer 312 illustrated as an open collar-like retaining and articulating structure; and a compression insert 314. The shank 304, the receiver 310 and the retainer 312 are substantially similar to the respective shank 4, receiver 10 and retainer 12 previously described herein with respect to the assembly 1. The receiver 310 is sized and proportioned slightly differently than the receiver 12 to cooperate with the insert 314. However, the receiver 310 otherwise includes the same component parts previously described herein with respect to the receiver 10. In particular, the receiver 310 includes a central axis H, a base 340, arms 342, a U-shaped channel 344, an interior surface with a guide and advancement structure 352, a pair of opposed apertures 354 upwardly and inwardly extending spring tabs 360, and an inner cavity 380 identical or substantially similar to the respective central axis B, base 40, arms 42, U-shaped channel 44, interior surface with a guide and advancement structure 52, apertures 54, upwardly and inwardly extending spring tabs 60 and inner cavity 80 of the receiver 10 of the assembly 1. The assembly 301 also cooperates with the rod 321 and a closure top 318 that are the same or similar to the respective rod 21 and closure top 18 previously described herein.

The compression or pressure insert 314 functions substantially similarly to the insert 14 previously described herein; however the insert 314 is of a different shape than the insert 14 and thus shall be described in detail herein.

The compression insert 314 is sized and shaped to be received by and uploaded into the receiver 310 at an opening into the cavity 380 at the base 340. In operation, the insert 314 is disposed between the rod 321 and the upper portion 308 of the bone screw shank 304. When the closure structure 318 presses upon the rod 321, the rod operatively presses upon the compression member 314 that in turn presses on the shank upper portion 308, but unlike the assemblies 1 and 101, the member 314 does not include a saddle. Therefore, rotational alignment of the rod 321 with the insert 314 is not necessary. However, because of the compact cylindrical shape of the insert 314, there is a possibility of the insert 314 becoming dislodged from a remainder of the assembly and undesirably moving up into the U-shaped channel 344 and out of the top of the receiver 310. Therefore, the receiver 310 equipped with spring tabs 360 prohibit undesirable upward movement of the insert 314 out of the receiver 310.

With particular reference to FIGS. 19-21, the compression insert 314 has an operational central axis that is the same as the central axis H of the receiver 310. The compression insert 314 has a central channel or through bore substantially defined by a an inner cylindrical surface 386 and an inner partially spherical surface 388. The insert through bore is sized and shaped to receive a driving tool (not shown) therethrough that engages a shank internal drive feature formed in the upper portion 308 when the shank is driven into bone. The surface 388 is sized and shaped to cooperate and mate with the spherical surface 330 of the shank upper portion 308 such that the surface 388 slidingly and pivotally mates with the spherical surface 330. The surface 388 may include a roughening or surface finish to aid in frictional contact between the surface 388 and the surface 330, once a desired angle of articulation of the shank 304 with respect to the retainer 312 and the receiver 310 is reached.

The compression insert 314 also includes a substantially planar top surface 390, a bottom surface 392 and an outer cylindrical surface 394. An outer angled surface or chamfer 395 is disposed between and connects the top surface 390 with the outer cylindrical surface 394. The cylindrical surface 394 is sized to be received within the cavity 380 of the receiver 310 and slidingly mate with a cylindrical inner surface 398 partially defining the cavity 380. The inner surface 398 is disposed directly below and adjacent to the spring tabs 360. Thus, the compression insert 314 ultimately seats on the shank upper portion 308 and is disposed at least partially in the channel 344 such that the compression insert 314 top surface 390 substantially contacts the rod 321 when the rod is placed in the receiver 310 and the closure structure 318 is tightened therein. With particular reference to FIG. 17, similar to the bottom surface 132 of the previously described insert 14, the bottom surface 392 of the insert 314 is sloped or angled to provide clearance for pivoting movement of the shank upper portion 308 and the retainer 312.

In operation, the tabs 360 may be bent inwardly toward the axis H before or after insertion of the insert 314 into the cavity 380, either by top or bottom loading. Preferably, the tabs 360 are initially bent inwardly toward the axis H, followed by bottom loading of the insert 314 into the cavity 380 at the cavity opening at the base 340. The shank 304 and the retainer 312 are then bottom loaded in a manner similar to what has been previously described herein with respect to the assembly 1. As best illustrated in FIG. 18, the tabs 360 engage the insert 314 at or near the chamfer 395, prohibiting further upward movement of the insert 314 into a remainder of the cavity 380. Eventually, the rod 321 and the closure top 318 are assembled with the receiver 310 in the manner described previously herein with respect to the receiver 10, rod 21 and closure top 18.

Figure 23:
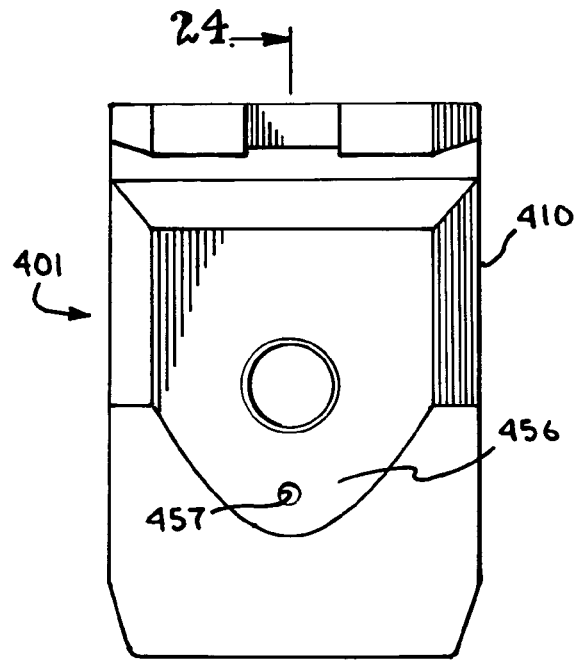
FIG. 23 is an enlarged and partial side elevational view of a fourth embodiment of a bone screw assembly according to the invention.
Figure 24:
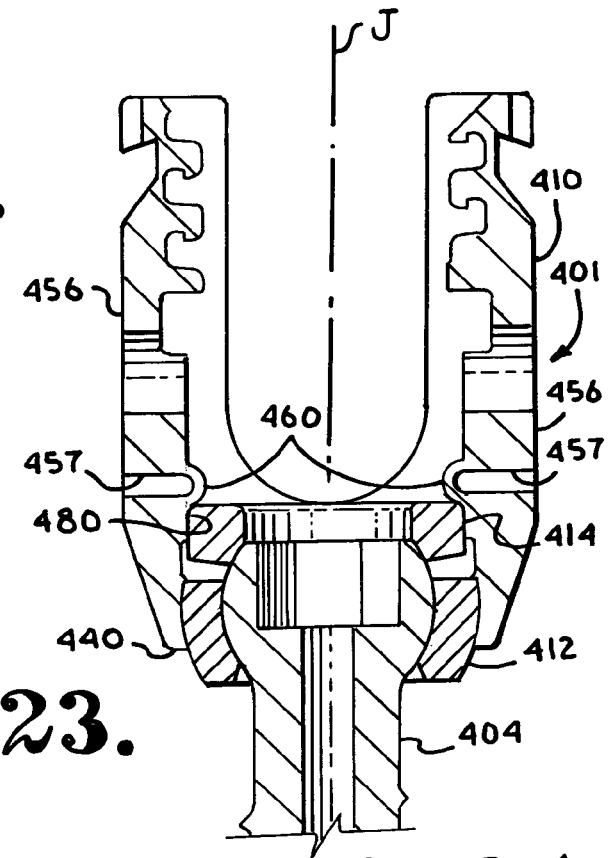
FIG. 24 is an enlarged and partial cross-sectional view taken along the line 24-24 of FIG. 23 showing a shank, a retainer, a compression insert and a receiver of the assembly of FIG. 23.

With reference to FIGS. 23 and 24, in a fourth embodiment according to the invention, generally 401, a receiver 410 is substantially identical to the receiver 310 of the assembly 301 with the exception that the spring tabs 360 are removed and replaced with a deformable material portion 460. The assembly 401 otherwise includes a shank 404, a retainer 412 and a compression insert 414 identical or substantially similar to the shank 304, retainer 312 and compression insert 314 previously described herein with respect to the assembly 301. Formed on outside surfaces 456 of the receiver 410 are a pair of opposed apertures 457. Each deformable portion or wall 460 partially defines the respective aperture 457. A tool (not shown) is inserted into the aperture and is pressed against the deformable portion 460, causing the portion 460 to extend into a cavity 480 of the receiver 410 in a direction towards a central axis J. Similar to the spring tabs 360, the now deformed wall portions 460 abut against and prohibit upward movement of the insert 414 and thus desirably retain the insert 414 in the cavity 480. If, as illustrated, the insert 414 is uploadable into the cavity 480 from an opening in the base 440 thereof, the portions 480 are preferably deformed prior to insertion of the insert 414 into the receiver 410. It is foreseen that in downloaded embodiments, the portions 480 may be deformed after downloading of the insert 414 into the cavity 480.

It is to be understood that while certain forms of the present invention have been illustrated and described herein, it is not to be limited to the specific forms or arrangement of parts described and shown.

What is claimed and desired to be secured by Letters Patent is as follows:

1. A polyaxial bone screw assembly comprising:
  a) a bone screw shank having an upper portion;
  b) a receiver having a cavity, the bone screw upper portion being receivable in the cavity;
  c) a retaining and articulating structure receivable in the cavity between the shank upper portion and the receiver, the retaining and articulating structure being unattached to both the shank and the receiver so as to be freely movable relative to both the shank and the receiver during positioning of the shank relative to the receiver;
  d) a compression insert disposed in the receiver during final positioning of the shank to lock the shank in place, the insert having a depression formed in an outer surface thereof and having a mating surface exclusively frictionally engageable with the bone screw upper portion, wherein the insert is spaced from the retaining and articulating structure; and
  e) resilient structure extending from the receiver and biasing against the compression insert at the depression thereof, the resilient structure resisting rotational movement of the compression insert within the receiver to maintain a desired alignment of the insert with the receiver, while allowing for upward and downward movement of the insert with respect to the receiver.

2. The assembly of claim 1 wherein the compression insert mating surface is concave and the bone screw upper portion is convex.

3. The assembly of claim 1 wherein the shank upper portion has a convex surface and the retaining and articulating structure has a concave surface in slidable mating engagement with the convex surface.

4. The assembly of claim 3 wherein the concave and convex surfaces are substantially spherical.

5. The assembly of claim 1 wherein the retaining and articulating structure has a convex surface and the receiver has a concave surface in slidable mating engagement with the convex surface.

6. The assembly of claim 5 wherein the concave and convex surfaces are substantially spherical.

7. The assembly of claim 1 wherein the shank upper portion has a tool engagement formation formed thereon adapted for non-slip engagement by a tool for driving the bone screw shank into bone.

8. The assembly of claim 7 wherein the tool engagement formation is a substantially hex shaped inner drive.

9. The assembly of claim 1 wherein the retaining and articulating structure is sized and shaped to be at least one of top-loadable and bottom-loadable into the receiver.

10. The assembly of claim 1 wherein the retaining and articulating structure further comprises first and second spaced ends, the retaining and articulating structure being compressible and expandable with the first and second ends being movable toward and away from one another.

11. The assembly of claim 10 wherein the retaining and articulating structure has a central axis, the first and second ends each being substantially planar surfaces running substantially parallel to the axis.

12. The assembly of claim 10 wherein the retaining and articulating structure has a central axis, the first and second ends each being substantially planar surfaces running at an angle oblique to the axis.

13. The assembly of claim 1 wherein the bone screw shank is cannulated.

14. The assembly of claim 1 wherein
  a) the bone screw shank has a body for fixation to bone, the shank body being integral with the shank upper portion; and
  b) the assembly further comprising a closure structure insertable into the receiver, the closure structure for operably urging the insert into frictional engagement with the bone screw shank upper portion and moving the shank in a direction to frictionally lock the position of the retaining and articulating structure with respect to the shank upper portion and the receiver, thereby locking the shank body in a selected angle with respect to the receiver.

15. The assembly of claim 14 wherein:
  (a) the receiver has upstanding spaced arms defining an open channel, the arms having guide and advancement structures on an inside surface thereof; and (b) the closure structure is sized and shaped to be positionable between the arms for closing the channel, the closure structure having a closure guide and advancement structure for rotatably mating with the guide and advancement structures on the arms, biasing the closure structure upon advancement rotation against a longitudinal connecting member disposed in the channel.

16. The assembly of claim 1 wherein the resilient structure is a pair of opposed spring tabs attached to the receiver and extending toward a central axis of the receiver.

17. The assembly of claim 16 wherein the spring tabs are integral with the receiver.

18. The assembly of claim 16 wherein the spring tabs are directed upwardly toward a top opening of the receiver.

19. The assembly of claim 16 wherein the spring tabs are directed downwardly toward a base of the receiver.

20. The assembly of claim 1 wherein the insert depression is a shallow groove.

21. The assembly of claim 1 wherein the insert depression is a flat surface.

22. The assembly of claim 1 wherein the insert is one of top and bottom loaded.

23. In a polyaxial bone screw assembly for surgical implantation and including a shank and a threaded body for inserting into a bone and a receiver having a channel for receiving a longitudinal connecting member within the channel, the improvement wherein:
   a) the shank has a first curvate surface at an upper end thereof and is pivotally engaged with an interior surface of the receiver; and further comprising:
   b) an articulation structure located between the shank upper end and the receiver, the articulation structure having a second curvate surface and an opposed third curvate surface, the articulation structure being in slidable engagement with receiver at the second curvate surface, the articulation structure third curvate surface being in slidable engagement with the shank upper end first curvate surface, the articulation structure being freely movable relative to both the shank and the receiver during positioning of the shank relative to the receiver;
   c) a compression insert having a fourth curvate surface in slidable engagement with the shank first curvate surface, the insert being spaced from the articulating structure, and the insert having a depression formed in an outer surface thereof; and
   d) resilient structure extending from the receiver and biasing against the compression insert at the depression thereof, the resilient structure resisting rotational movement of the compression insert within the receiver to maintain a desired alignment of the insert with the receiver, while allowing for upward and downward movement of the insert with respect to the receiver.

24. The improvement of claim 23 wherein the shank upper end has a tool engagement formation formed thereon adapted for non-slip engagement by a tool for driving the bone screw shank into bone.

25. The improvement of claim 23 wherein the articulation structure is sized and shaped to be at least one of top-loadable and bottom-loadable into the receiver.

26. The improvement of claim 23 wherein the articulation structure further comprises first and second spaced ends, the articulation structure being compressible and expandable with the first and second ends being movable toward and away from one another.

27. The improvement of claim 23 wherein the resilient structure is a pair of opposed spring tabs integral with the receiver and extending toward a central axis of the receiver.

28. The improvement of claim 27 wherein the opposed spring tabs face downwardly.

29. The improvement of claim 27 wherein the opposed spring tabs face upwardly.

30. In a bone screw assembly having a receiver pivotally connected to a bone screw shank, the receiver having an opening for receiving a longitudinal connecting member and a compression insert disposed in the receiver for frictional engagement with the longitudinal connection member and having a depression formed in an outer surface thereof, the improvement comprising:
   a) resilient structure extending from the receiver and biasing against the compression insert at the depression thereof, the resilient structure resisting rotational movement of the compression insert within the receiver to maintain a desired alignment of the insert with the receiver, while allowing for upward and downward movement of the insert with respect to the receiver; and
   b) an articulation structure disposed between the bone screw shank and the receiver, the articulation structure having a first curvate wall in sliding engagement with the receiver and a second curvate wall in sliding engagement with the bone screw shank.

31. The improvement of claim 30 wherein the resilient structure is a pair of opposed spring tabs attached to the receiver and extending toward a central axis of the receiver.

32. The improvement of claim 31 wherein the opposed spring tabs face downwardly.

33. The improvement of claim 31 wherein the opposed spring tabs face upwardly.

34. The improvement of claim 30 wherein the insert depression is a shallow groove.

35. The improvement of claim 30 wherein the insert depression is a flat surface.

36. The improvement of claim 30 wherein the articulation structure further comprises first and second spaced ends, the articulation structure being compressible and expandable with the first and second ends being movable toward and away from one another.

37. The improvement of claim 30 wherein the articulation structure is freely movable relative to both the shank and the receiver during positioning of the shank relative to the receiver.

38. In a bone screw assembly having a receiver pivotally connected to a bone screw shank, the shank having a lower portion attachable to a bone and an upper head portion, the receiver having an opening for receiving a longitudinal connecting member, the assembly also having a compression insert disposed in the receiver for frictional engagement with the longitudinal connecting member and the shank upper head portion, the improvement wherein the receiver comprises:
   a resilient structure integral with the receiver, the structure having a surface projecting inwardly and facing downwardly into the receiver in a direction towards the shank; the structure biasing against the compression insert, holding the insert within the receiver and downwardly against the shank upper head portion, and resisting rotational movement of the insert to maintain a desired alignment of the insert with the receiver, while allowing for upward and downward movement of the insert with respect to the receiver.

39. The improvement of claim 38 wherein the resilient structure is a first resilient structure; and further comprising a second resilient structure integral with the receiver and located opposite the first resilient structure, the second resilient structure also projecting inwardly and facing downwardly into the receiver in a direction towards the shank.

40. In a bone screw assembly having a receiver pivotally connected to a bone screw shank, the shank having a lower portion attachable to a bone and an upper head portion, the receiver having an opening for receiving a longitudinal connecting member, the assembly also having a compression insert disposed in the receiver for frictional engagement with the longitudinal connecting member and the shank upper head portion, the improvement wherein the receiver comprises:
- a resilient structure integral with the receiver, the structure having a surface projecting inwardly and facing upwardly into the receiver in a direction towards the shank; the structure biasing against the compression insert, holding the insert within the receiver and downwardly against the shank upper head portion, and resisting rotational movement of the insert to maintain a desired alignment of the insert with the receiver, while allowing for upward and downward movement of the insert with respect to the receiver.

41. The improvement of claim 40, wherein the resilient structure is a first resilient structure; and further comprising a second resilient structure integral with the receiver and located opposite the first resilient structure, the second resilient structure also projecting inwardly and facing upwardly into the receiver in a direction towards the shank.

42. In a bone screw assembly having a receiver pivotally connected to a bone screw shank, the receiver having an opening for receiving a longitudinal connecting member and a compression insert disposed in the receiver for frictional engagement with the longitudinal connection member, the improvement comprising:
- a) resilient structure extending from the receiver and biasing against the compression insert at a depression formed in a surface of the insert, the resilient structure resisting rotational movement of the compression insert within the receiver to maintain a desired alignment of the insert with the receiver, while allowing for upward and downward movement of the insert with respect to the receiver; and
- b) an articulation structure disposed between the bone screw shank and the receiver, the articulation structure having a first curvate wall in sliding engagement with the receiver and a second curvate wall in sliding engagement with the bone screw shank; and
- c) the compression insert comprising a top and bottom portion having a bottom surface and a through-bore with an opening on the bottom surface sized and shaped to mate with an upper portion of the bone screw shank.

43. The improvement of claim 42, wherein the top portion of the through-bore is cylindrical shaped, and the bottom portion of the through-bore is sized and shaped to mate with the upper portion of the bone screw shank.

44. A polyaxial bone screw assembly comprising:
- a) a bone screw shank having an upper portion with a top surface;
- b) a receiver having an internal cavity with an integral spherical seating surface adjacent a lower opening, the bone screw upper portion receivable in the cavity through the opening;
- c) a retaining and articulating structure receivable in the cavity and positioned below the top surface of the shank and between the shank upper portion and the receiver, the retaining and articulating structure having an outer spherical surface for seating against the receiver seating surface and being unattached to both the shank and the receiver so as to be freely movable relative to both the shank and the receiver during positioning of the shank relative to the receiver;
- d) a compression insert disposed in the receiver during final positioning of the shank to lock the shank in place, the insert having a lower first mating surface frictionally engageable with the bone screw upper portion and an upper second mating surface to engage a rod; and
- e) resilient structure extending from the receiver and biasing against the compression insert at a depression formed in a surface of the insert, the resilient structure resisting rotational movement of the compression insert within the receiver to maintain a desired alignment of the insert with the receiver, while allowing for upward and downward movement of the insert with respect to the receiver.

* * * * *